(12) United States Patent
Watarai et al.

(10) Patent No.: US 8,454,955 B2
(45) Date of Patent: Jun. 4, 2013

(54) METHODS FOR TREATING ALLERGIC AIRWAY INFLAMMATION, AIRWAY HYPERSENSITIVITY, AND EOSINOPHILIA

(75) Inventors: Hiroshi Watarai, Kanagawa (JP); Masaru Taniguchi, Kanagawa (JP)

(73) Assignee: Riken, Wako-shi (JP)

( * ) Notice: Subject to any disclaimer, the term of this patent is extended or adjusted under 35 U.S.C. 154(b) by 0 days.

(21) Appl. No.: 12/745,139

(22) PCT Filed: Aug. 29, 2008

(86) PCT No.: PCT/JP2008/065569
§ 371 (c)(1),
(2), (4) Date: Nov. 15, 2010

(87) PCT Pub. No.: WO2009/069355
PCT Pub. Date: Jun. 4, 2009

(65) Prior Publication Data
US 2011/0052598 A1   Mar. 3, 2011

(30) Foreign Application Priority Data
Nov. 28, 2007 (JP) .................................. 2007-307981

(51) Int. Cl.
*A61K 39/395* (2006.01)
(52) U.S. Cl.
USPC .......................... 424/130.1; 530/350; 530/351
(58) Field of Classification Search
None
See application file for complete search history.

(56) References Cited

U.S. PATENT DOCUMENTS

2003/0165460 A1* 9/2003 Hurst et al. .................. 424/85.2
2004/0043397 A1* 3/2004 Chen et al. ........................ 435/6

FOREIGN PATENT DOCUMENTS

WO    WO 01/57202 A2    8/2001

OTHER PUBLICATIONS

Meyer et al., iNKT cells in allergic disease. Curr Top Microbiol Immunol. 2007;314:269-91.*
Oki et al. Invariant Natural Killer T (iNKT) Cells in Asthma: A Novel Insight into the Pathogenesis of Asthma and the Therapeutic Implication of Glycolipid Ligands for Allergic Diseases. Allergology Internatinal. 2007;56:7-14.*
Angkasekwinai et al., *J. Exp. Med.*, 204(7): 1509-1517 (2007).
Akbari et al., *Nature Medicine*, 9(5): 582-588 (2003).
Ballantyne et al., *J. Allergy Clin. Immunol.*, 120(6): 1324-1331 (2007).
Fort et al., *Immunity*, 15(6): 985-995 (2001).
Lee et al., *The Journal of Biological Chemistry*, 276(2): 1660-1664 (2001).
Tian et al., *Oncogene*, 19(17): 2098-2109 (2000).
Umetsu et al., *Nature Reviews Immunology*, 6(12): 953-958 (2006).
Wang et al., *J. Exp. Med.*, 204(8): 1837-1847 (2007).

* cited by examiner

*Primary Examiner* — Dong Jiang
(74) *Attorney, Agent, or Firm* — Leydig, Voit & Mayer, Ltd.

(57) ABSTRACT

The invention provides a method of screening a therapeutic agent for allergic airway inflammation and/or airway hypersensitivity, comprising using an IL-17RB positive NKT cell, as well as a therapeutic agent for allergic airway inflammation and/or airway hypersensitivity, containing a substance capable of inhibiting or eliminating the Th2 cell-like function of an IL-17RB positive NKT cell as an active ingredient.

5 Claims, 21 Drawing Sheets

DTT− (dimer): 140 kDa
DTT+ (monomer): 70 kDa

IL-17RB-transfected HEK293T

SEQUENCE LISTING

```
<160> NUMBER OF SEQ ID NOS: 52

<210> SEQ ID NO 1
<211> LENGTH: 2062
<212> TYPE: DNA
<213> ORGANISM: Mus musculus
<220> FEATURE:
<221> NAME/KEY: CDS
<222> LOCATION: (107)..(1606)

<400> SEQUENCE: 1
ggtgggaggc ggagcccgga gaactgcggc gggcgcctgg ataagaggac cctggacctc        60
tggccccagc tccgcgtggt ggtgggcggt ggccagtggc cgggcc atg ttg cta         115
                                                    Met Leu Leu
                                                     1 gtg ttg ctg atc ttg gct gca tcg tgc agg agc gcc ctg cct cga gag        163
Val Leu Leu Ile Leu Ala Ala Ser Cys Arg Ser Ala Leu Pro Arg Glu
      5                  10                  15 ccg act att cag tgt ggc tct gag aca ggg cca tct cca gag tgg atg        211
Pro Thr Ile Gln Cys Gly Ser Glu Thr Gly Pro Ser Pro Glu Trp Met
 20                  25                  30                  35 gtc caa cac aca ctc act cca gga gac ttg agg gac ctc caa gtg gaa        259
Val Gln His Thr Leu Thr Pro Gly Asp Leu Arg Asp Leu Gln Val Glu
                 40                  45                  50 ctc gtc aag aca agt gtg gca gca gag gag ttt tca att ttg atg aac        307
Leu Val Lys Thr Ser Val Ala Ala Glu Glu Phe Ser Ile Leu Met Asn
             55                  60                  65 ata agc tgg ata ctc cgg gca gac gcc agc atc cgc ttg ttg aag gcc        355
Ile Ser Trp Ile Leu Arg Ala Asp Ala Ser Ile Arg Leu Leu Lys Ala
         70                  75                  80 acc aag atc tgc gtg agt ggc aaa aac aac atg aat tca tac agc tgt        403
Thr Lys Ile Cys Val Ser Gly Lys Asn Asn Met Asn Ser Tyr Ser Cys
     85                  90                  95 gtg agg tgc aac tac aca gag gcc ttc caa agc cag acc aga cct tcc        451
Val Arg Cys Asn Tyr Thr Glu Ala Phe Gln Ser Gln Thr Arg Pro Ser
100                 105                 110                 115 ggc ggc aaa tgg aca ttc tcc tat gta ggc ttc cct gtg gag ctg agc        499
Gly Gly Lys Trp Thr Phe Ser Tyr Val Gly Phe Pro Val Glu Leu Ser
                 120                 125                 130 act ctc tat ctc atc agc gcc cat aac atc ccc aat gct aat atg aat        547
Thr Leu Tyr Leu Ile Ser Ala His Asn Ile Pro Asn Ala Asn Met Asn
             135                 140                 145 gag gac agc cct tct ttg tct gtg aac ttc acc tcg cca ggc tgc cta        595
Glu Asp Ser Pro Ser Leu Ser Val Asn Phe Thr Ser Pro Gly Cys Leu
         150                 155                 160 aac cac gta atg aaa tat aaa aag cag tgc act gag gcg gga agc ctg        643
Asn His Val Met Lys Tyr Lys Lys Gln Cys Thr Glu Ala Gly Ser Leu
     165                 170                 175 tgg gac cca gac atc act gct tgt aaa aag aac gag aag atg gtt gaa        691
Trp Asp Pro Asp Ile Thr Ala Cys Lys Lys Asn Glu Lys Met Val Glu
180                 185                 190                 195
```

```
gtg aat ttc aca acc aat ccc ctt gga aac aga tac acg att ctc att    739
Val Asn Phe Thr Thr Asn Pro Leu Gly Asn Arg Tyr Thr Ile Leu Ile
                200                 205                 210 caa cgg gac acg aca ttg ggg ttt tct aga gtg ctg gag aat aaa ctg    787
Gln Arg Asp Thr Thr Leu Gly Phe Ser Arg Val Leu Glu Asn Lys Leu
            215                 220                 225 atg agg acg tct gta gcc atc ccg gtg act gag gag agt gaa ggt gcg    835
Met Arg Thr Ser Val Ala Ile Pro Val Thr Glu Glu Ser Glu Gly Ala
        230                 235                 240 gtg gtt cag ctg acc cca tat tta cat acc tgc ggc aat gac tgc atc    883
Val Val Gln Leu Thr Pro Tyr Leu His Thr Cys Gly Asn Asp Cys Ile
    245                 250                 255 cga cgc gaa ggg aca gtt gtg ctt tgc tca gag aca agt gct ccc atc    931
Arg Arg Glu Gly Thr Val Val Leu Cys Ser Glu Thr Ser Ala Pro Ile
260                 265                 270                 275 cct cca gat gac aac aga cgc atg ctg gga ggc tgg ctg cct ctc ttc    979
Pro Pro Asp Asp Asn Arg Arg Met Leu Gly Gly Trp Leu Pro Leu Phe
                280                 285                 290 ctg gtg ctg ctg gtg gct gtg tgg gtg ctg gca gct ggg atc tac cta   1027
Leu Val Leu Leu Val Ala Val Trp Val Leu Ala Ala Gly Ile Tyr Leu
            295                 300                 305 act tgg agg caa gga agg agc acg aag acg tcc ttt cct att tcc acc   1075
Thr Trp Arg Gln Gly Arg Ser Thr Lys Thr Ser Phe Pro Ile Ser Thr
        310                 315                 320 atg ctc ctg ccc ctc att aag gtc ctg gtg gtt tat cct tct gag ata   1123
Met Leu Leu Pro Leu Ile Lys Val Leu Val Val Tyr Pro Ser Glu Ile
    325                 330                 335 tgt ttc cat cac acc gtc tgt cgc ttc act gac ttt ctt caa aac tac   1171
Cys Phe His His Thr Val Cys Arg Phe Thr Asp Phe Leu Gln Asn Tyr
340                 345                 350                 355 tgc aga agt gag gtc atc ctt gaa aaa tgg cag aaa aag aaa atc gcc   1219
Cys Arg Ser Glu Val Ile Leu Glu Lys Trp Gln Lys Lys Lys Ile Ala
                360                 365                 370 gag atg ggg ccg gta cag tgg ctg acc act cag aag caa gcg gca gat   1267
Glu Met Gly Pro Val Gln Trp Leu Thr Thr Gln Lys Gln Ala Ala Asp
            375                 380                 385 aaa gtg gtc ttc ctt ctt ccc agt gac gtc ccg acc ctt tgt gac agt   1315
Lys Val Val Phe Leu Leu Pro Ser Asp Val Pro Thr Leu Cys Asp Ser
        390                 395                 400 gcc tgt ggc cac aat gag ggc agc gcc agg gag aac tct cag gat ctg   1363
Ala Cys Gly His Asn Glu Gly Ser Ala Arg Glu Asn Ser Gln Asp Leu
    405                 410                 415 ttc cct ctt gcc ttt aac ctc ttt tgt agt gat ttc agc agc cag acg   1411
Phe Pro Leu Ala Phe Asn Leu Phe Cys Ser Asp Phe Ser Ser Gln Thr
420                 425                 430                 435 cat ctg cac aaa tac ctg gtg gtc tat ctt ggg gga gca gac ctc aaa   1459
His Leu His Lys Tyr Leu Val Val Tyr Leu Gly Gly Ala Asp Leu Lys
                440                 445                 450 ggc gac tat aat gcc ctg agt gtc tgc ccc caa tat cat ctc atg aag   1507
Gly Asp Tyr Asn Ala Leu Ser Val Cys Pro Gln Tyr His Leu Met Lys
            455                 460                 465 gac gcc aca gct ttc cac aca gaa ctt ctc aag gct acg cag agc atg   1555
Asp Ala Thr Ala Phe His Thr Glu Leu Leu Lys Ala Thr Gln Ser Met
        470                 475                 480 tca gtg aag aaa cgc tca caa gcc tgc cat gat agc tgt tca ccc ttg   1603
Ser Val Lys Lys Arg Ser Gln Ala Cys His Asp Ser Cys Ser Pro Leu
    485                 490                 495 tag tccacccggg ggaatagaga ctctgaagcc ttcctactct cccttccagt        1656
gacaaatgct gtgtgacgac tctgaaatgt gtgggagagg ctgtgtggag gtagtgctat 1716
```

-continued

```
gtacaaactt gctttaaaac tggagtttgc aaagtcaacc tgagcataca cgcctgaggc    1776
tagtcattgg ctggatttat gaagacaaca cagttacaga caataatgag tgggacctac    1836
atttgggata tacccaaagc tgggtaatga ttatcactga gaaccacgca ctctggccat    1896
gaggtaatac ggcacttccc tgtcaggctg tctgtcaggt tgggtctgtc ttgcactgcc    1956
catgctctat gctgcacgta gaccgttttg taacatttta atctgttaat gaataatccg    2016
tttgggaggc tctcactaat gtgtagcttc ctaagagaag aagcct                    2062
```

<210> SEQ ID NO 2
<211> LENGTH: 499
<212> TYPE: PRT
<213> ORGANISM: Mus musculus

<400> SEQUENCE: 2

```
Met Leu Leu Val Leu Ile Leu Ala Ala Ser Cys Arg Ser Ala Leu
1               5                   10                  15

Pro Arg Glu Pro Thr Ile Gln Cys Gly Ser Glu Thr Gly Pro Ser Pro
            20                  25                  30

Glu Trp Met Val Gln His Thr Leu Thr Pro Gly Asp Leu Arg Asp Leu
        35                  40                  45

Gln Val Glu Leu Val Lys Thr Ser Val Ala Ala Glu Glu Phe Ser Ile
    50                  55                  60

Leu Met Asn Ile Ser Trp Ile Leu Arg Ala Asp Ala Ser Ile Arg Leu
65                  70                  75                  80

Leu Lys Ala Thr Lys Ile Cys Val Ser Gly Lys Asn Asn Met Asn Ser
                85                  90                  95

Tyr Ser Cys Val Arg Cys Asn Tyr Thr Glu Ala Phe Gln Ser Gln Thr
            100                 105                 110

Arg Pro Ser Gly Gly Lys Trp Thr Phe Ser Tyr Val Gly Phe Pro Val
        115                 120                 125

Glu Leu Ser Thr Leu Tyr Leu Ile Ser Ala His Asn Ile Pro Asn Ala
    130                 135                 140

Asn Met Asn Glu Asp Ser Pro Ser Leu Ser Val Asn Phe Thr Ser Pro
145                 150                 155                 160

Gly Cys Leu Asn His Val Met Lys Tyr Lys Lys Gln Cys Thr Glu Ala
                165                 170                 175

Gly Ser Leu Trp Asp Pro Asp Ile Thr Ala Cys Lys Lys Asn Glu Lys
            180                 185                 190

Met Val Glu Val Asn Phe Thr Thr Asn Pro Leu Gly Asn Arg Tyr Thr
        195                 200                 205

Ile Leu Ile Gln Arg Asp Thr Thr Leu Gly Phe Ser Arg Val Leu Glu
    210                 215                 220

Asn Lys Leu Met Arg Thr Ser Val Ala Ile Pro Val Thr Glu Glu Ser
225                 230                 235                 240

Glu Gly Ala Val Val Gln Leu Thr Pro Tyr Leu His Thr Cys Gly Asn
                245                 250                 255

Asp Cys Ile Arg Arg Glu Gly Thr Val Val Leu Cys Ser Glu Thr Ser
            260                 265                 270

Ala Pro Ile Pro Pro Asp Asp Asn Arg Arg Met Leu Gly Gly Trp Leu
        275                 280                 285

Pro Leu Phe Leu Val Leu Leu Val Ala Val Trp Val Leu Ala Ala Gly
    290                 295                 300

Ile Tyr Leu Thr Trp Arg Gln Gly Arg Ser Thr Lys Thr Ser Phe Pro
305                 310                 315                 320
```

```
Ile Ser Thr Met Leu Leu Pro Leu Ile Lys Val Leu Val Tyr Pro
            325                 330                 335

Ser Glu Ile Cys Phe His His Thr Val Cys Arg Phe Thr Asp Phe Leu
            340                 345                 350

Gln Asn Tyr Cys Arg Ser Glu Val Ile Leu Glu Lys Trp Gln Lys Lys
            355                 360                 365

Lys Ile Ala Glu Met Gly Pro Val Gln Trp Leu Thr Thr Gln Lys Gln
            370                 375                 380

Ala Ala Asp Lys Val Val Phe Leu Leu Pro Ser Asp Val Pro Thr Leu
385                 390                 395                 400

Cys Asp Ser Ala Cys Gly His Asn Glu Gly Ser Ala Arg Glu Asn Ser
            405                 410                 415

Gln Asp Leu Phe Pro Leu Ala Phe Asn Leu Phe Cys Ser Asp Phe Ser
            420                 425                 430

Ser Gln Thr His Leu His Lys Tyr Leu Val Val Tyr Leu Gly Gly Ala
            435                 440                 445

Asp Leu Lys Gly Asp Tyr Asn Ala Leu Ser Val Cys Pro Gln Tyr His
            450                 455                 460

Leu Met Lys Asp Ala Thr Ala Phe His Thr Glu Leu Leu Lys Ala Thr
465                 470                 475                 480

Gln Ser Met Ser Val Lys Lys Arg Ser Gln Ala Cys His Asp Ser Cys
            485                 490                 495

Ser Pro Leu

<210> SEQ ID NO 3
<211> LENGTH: 1654
<212> TYPE: DNA
<213> ORGANISM: Artificial Sequence
<220> FEATURE:
<223> OTHER INFORMATION: Fusion protein of IL-17RB extracellular domain
      and human IgG1 Fc region
<220> FEATURE:
<221> NAME/KEY: CDS
<222> LOCATION: (107)..(1654)

<400> SEQUENCE: 3
ggtgggaggc ggagcccgga gaactgcggc gggcgcctgg ataagaggac cctggacctc    60
tggccccagc tccgcgtggt ggtgggcggt ggccagtggc cgggcc atg ttg cta      115
                                                  Met Leu Leu
                                                  1 gtg ttg ctg atc ttg gct gca tcg tgc agg agc gcc ctg cct cga gag    163
Val Leu Leu Ile Leu Ala Ala Ser Cys Arg Ser Ala Leu Pro Arg Glu
    5                  10                  15 ccg act att cag tgt ggc tct gag aca ggg cca tct cca gag tgg atg    211
Pro Thr Ile Gln Cys Gly Ser Glu Thr Gly Pro Ser Pro Glu Trp Met
20                  25                  30                  35 gtc caa cac aca ctc act cca gga gac ttg agg gac ctc caa gtg gaa    259
Val Gln His Thr Leu Thr Pro Gly Asp Leu Arg Asp Leu Gln Val Glu
                40                  45                  50 ctc gtc aag aca agt gtg gca gca gag gag ttt tca att ttg atg aac    307
Leu Val Lys Thr Ser Val Ala Ala Glu Glu Phe Ser Ile Leu Met Asn
            55                  60                  65 ata agc tgg ata ctc cgg gca gac gcc agc atc cgc ttg ttg aag gcc    355
Ile Ser Trp Ile Leu Arg Ala Asp Ala Ser Ile Arg Leu Leu Lys Ala
        70                  75                  80 acc aag atc tgc gtg agt ggc aaa aac aac atg aat tca tac agc tgt    403
Thr Lys Ile Cys Val Ser Gly Lys Asn Asn Met Asn Ser Tyr Ser Cys
85                  90                  95 gtg agg tgc aac tac aca gag gcc ttc caa agc cag acc aga cct tcc    451
```

```
Val Arg Cys Asn Tyr Thr Glu Ala Phe Gln Ser Gln Thr Arg Pro Ser
100                 105                 110                 115 ggc ggc aaa tgg aca ttc tcc tat gta ggc ttc cct gtg gag ctg agc       499
Gly Gly Lys Trp Thr Phe Ser Tyr Val Gly Phe Pro Val Glu Leu Ser
            120                 125                 130 act ctc tat ctc atc agc gcc cat aac atc ccc aat gct aat atg aat       547
Thr Leu Tyr Leu Ile Ser Ala His Asn Ile Pro Asn Ala Asn Met Asn
                135                 140                 145 gag gac agc cct tct ttg tct gtg aac ttc acc tcg cca ggc tgc cta       595
Glu Asp Ser Pro Ser Leu Ser Val Asn Phe Thr Ser Pro Gly Cys Leu
            150                 155                 160 aac cac gta atg aaa tat aaa aag cag tgc act gag gcg gga agc ctg       643
Asn His Val Met Lys Tyr Lys Lys Gln Cys Thr Glu Ala Gly Ser Leu
165                 170                 175 tgg gac cca gac atc act gct tgt aaa aag aac gag aag atg gtt gaa       691
Trp Asp Pro Asp Ile Thr Ala Cys Lys Lys Asn Glu Lys Met Val Glu
180                 185                 190                 195 gtg aat ttc aca acc aat ccc ctt gga aac aga tac acg att ctc att       739
Val Asn Phe Thr Thr Asn Pro Leu Gly Asn Arg Tyr Thr Ile Leu Ile
                200                 205                 210 caa cgg gac acg aca ttg ggg ttt tct aga gtg ctg gag aat aaa ctg       787
Gln Arg Asp Thr Thr Leu Gly Phe Ser Arg Val Leu Glu Asn Lys Leu
            215                 220                 225 atg agg acg tct gta gcc atc ccg gtg act gag gag agt gaa ggt gcg       835
Met Arg Thr Ser Val Ala Ile Pro Val Thr Glu Glu Ser Glu Gly Ala
        230                 235                 240 gtg gtt cag ctg acc cca tat tta cat acc tgc ggc aat gac tgc atc       883
Val Val Gln Leu Thr Pro Tyr Leu His Thr Cys Gly Asn Asp Cys Ile
245                 250                 255 cga cgc gaa ggg aca gtt gtg ctt tgc tca gag aca agt gct ccc atc       931
Arg Arg Glu Gly Thr Val Val Leu Cys Ser Glu Thr Ser Ala Pro Ile
260                 265                 270                 275 cct cca gat gac aac aga cgc gaa ttc ccc aaa tct tgt gac aaa act       979
Pro Pro Asp Asp Asn Arg Arg Glu Phe Pro Lys Ser Cys Asp Lys Thr
                280                 285                 290 cac aca tgc cca ccg tgc cca gca cct gaa gcc gag ggg gga ccg tca      1027
His Thr Cys Pro Pro Cys Pro Ala Pro Glu Ala Glu Gly Gly Pro Ser
            295                 300                 305 gtc ttc ctc ttc ccc cca aaa ccc aag gac acc ctc atg atc tcc cgg      1075
Val Phe Leu Phe Pro Pro Lys Pro Lys Asp Thr Leu Met Ile Ser Arg
        310                 315                 320 acc cct gag gtc aca tgc gtg gtg gtg gac gtg agc cac gaa gac cct      1123
Thr Pro Glu Val Thr Cys Val Val Val Asp Val Ser His Glu Asp Pro
325                 330                 335 gag gtc aag ttc aac tgg tac gtg gac ggc gtg gag gtg cat aat gcc      1171
Glu Val Lys Phe Asn Trp Tyr Val Asp Gly Val Glu Val His Asn Ala
340                 345                 350                 355 aag aca aag ccg cgg gag gag cag tac aac agc acg tac cgt gtg gtc      1219
Lys Thr Lys Pro Arg Glu Glu Gln Tyr Asn Ser Thr Tyr Arg Val Val
                360                 365                 370 agc gtc ctc acc gtc ctg cac cag gac tgg ctg aat ggc aag gag tac      1267
Ser Val Leu Thr Val Leu His Gln Asp Trp Leu Asn Gly Lys Glu Tyr
            375                 380                 385 aag tgc aag gtc tcc aac aaa gcc ctc cca gcc ccc atc gag aaa acc      1315
Lys Cys Lys Val Ser Asn Lys Ala Leu Pro Ala Pro Ile Glu Lys Thr
        390                 395                 400 atc tcc aaa gcc aaa ggg cag ccc cga gaa cca cag gtg tac acc ctg      1363
Ile Ser Lys Ala Lys Gly Gln Pro Arg Glu Pro Gln Val Tyr Thr Leu
405                 410                 415 ccc cca tcc cgg gat gag ctg acc aag aac cag gtc agc ctg acc tgc      1411
```

```
                Pro Pro Ser Arg Asp Glu Leu Thr Lys Asn Gln Val Ser Leu Thr Cys
                420                 425                 430                 435 ctg gtc aaa ggc ttc tat ccc agc gac atc gcc gtg gag tgg gag agc          1459
Leu Val Lys Gly Phe Tyr Pro Ser Asp Ile Ala Val Glu Trp Glu Ser
                440                 445                 450 aat ggg cag ccg gag aac aac tac aag acc acg cct ccc gtg ctg gac          1507
Asn Gly Gln Pro Glu Asn Asn Tyr Lys Thr Thr Pro Pro Val Leu Asp
                455                 460                 465 tcc gac ggc tcc ttc ttc ctc tac agc aag ctc acc gtg gac aag agc          1555
Ser Asp Gly Ser Phe Phe Leu Tyr Ser Lys Leu Thr Val Asp Lys Ser
                470                 475                 480 agg tgg cag cag ggg aac gtc ttc tca tgc tcc gtg atg cat gag gct          1603
Arg Trp Gln Gln Gly Asn Val Phe Ser Cys Ser Val Met His Glu Ala
485                 490                 495 ctg cac aac cac tac acg cag aag agc ctc tcc ctg tct ccg ggt aaa          1651
Leu His Asn His Tyr Thr Gln Lys Ser Leu Ser Leu Ser Pro Gly Lys
500                 505                 510                 515 tga                                                                       1654
```

<210> SEQ ID NO 4
<211> LENGTH: 515
<212> TYPE: PRT
<213> ORGANISM: Artificial Sequence
<220> FEATURE:
<223> OTHER INFORMATION: Fusion protein of IL-17RB extracellular domain
      and human IgG1 Fc region

<400> SEQUENCE: 4

```
Met Leu Leu Val Leu Leu Ile Leu Ala Ala Ser Cys Arg Ser Ala Leu
1               5                   10                  15

Pro Arg Glu Pro Thr Ile Gln Cys Gly Ser Glu Thr Gly Pro Ser Pro
            20                  25                  30

Glu Trp Met Val Gln His Thr Leu Thr Pro Gly Asp Leu Arg Asp Leu
        35                  40                  45

Gln Val Glu Leu Val Lys Thr Ser Val Ala Ala Glu Glu Phe Ser Ile
    50                  55                  60

Leu Met Asn Ile Ser Trp Ile Leu Arg Ala Asp Ala Ser Ile Arg Leu
65                  70                  75                  80

Leu Lys Ala Thr Lys Ile Cys Val Ser Gly Lys Asn Asn Met Asn Ser
                85                  90                  95

Tyr Ser Cys Val Arg Cys Asn Tyr Thr Glu Ala Phe Gln Ser Gln Thr
            100                 105                 110

Arg Pro Ser Gly Gly Lys Trp Thr Phe Ser Tyr Val Gly Phe Pro Val
        115                 120                 125

Glu Leu Ser Thr Leu Tyr Leu Ile Ser Ala His Asn Ile Pro Asn Ala
    130                 135                 140

Asn Met Asn Glu Asp Ser Pro Ser Leu Ser Val Asn Phe Thr Ser Pro
145                 150                 155                 160

Gly Cys Leu Asn His Val Met Lys Tyr Lys Lys Gln Cys Thr Glu Ala
                165                 170                 175

Gly Ser Leu Trp Asp Pro Asp Ile Thr Ala Cys Lys Lys Asn Glu Lys
            180                 185                 190

Met Val Glu Val Asn Phe Thr Thr Asn Pro Leu Gly Asn Arg Tyr Thr
        195                 200                 205

Ile Leu Ile Gln Arg Asp Thr Thr Leu Gly Phe Ser Arg Val Leu Glu
    210                 215                 220

Asn Lys Leu Met Arg Thr Ser Val Ala Ile Pro Val Thr Glu Glu Ser
225                 230                 235                 240
```

```
Glu Gly Ala Val Val Gln Leu Thr Pro Tyr Leu His Thr Cys Gly Asn
                245                 250                 255

Asp Cys Ile Arg Arg Glu Gly Thr Val Val Leu Cys Ser Glu Thr Ser
            260                 265                 270

Ala Pro Ile Pro Pro Asp Asp Asn Arg Arg Glu Phe Pro Lys Ser Cys
        275                 280                 285

Asp Lys Thr His Thr Cys Pro Pro Cys Pro Ala Pro Glu Ala Glu Gly
    290                 295                 300

Gly Pro Ser Val Phe Leu Phe Pro Pro Lys Pro Lys Asp Thr Leu Met
305                 310                 315                 320

Ile Ser Arg Thr Pro Glu Val Thr Cys Val Val Val Asp Val Ser His
                325                 330                 335

Glu Asp Pro Glu Val Lys Phe Asn Trp Tyr Val Asp Gly Val Glu Val
            340                 345                 350

His Asn Ala Lys Thr Lys Pro Arg Glu Glu Gln Tyr Asn Ser Thr Tyr
        355                 360                 365

Arg Val Val Ser Val Leu Thr Val Leu His Gln Asp Trp Leu Asn Gly
    370                 375                 380

Lys Glu Tyr Lys Cys Lys Val Ser Asn Lys Ala Leu Pro Ala Pro Ile
385                 390                 395                 400

Glu Lys Thr Ile Ser Lys Ala Lys Gly Gln Pro Arg Glu Pro Gln Val
                405                 410                 415

Tyr Thr Leu Pro Pro Ser Arg Asp Glu Leu Thr Lys Asn Gln Val Ser
            420                 425                 430

Leu Thr Cys Leu Val Lys Gly Phe Tyr Pro Ser Asp Ile Ala Val Glu
        435                 440                 445

Trp Glu Ser Asn Gly Gln Pro Glu Asn Asn Tyr Lys Thr Thr Pro Pro
    450                 455                 460

Val Leu Asp Ser Asp Gly Ser Phe Phe Leu Tyr Ser Lys Leu Thr Val
465                 470                 475                 480

Asp Lys Ser Arg Trp Gln Gln Gly Asn Val Phe Ser Cys Ser Val Met
                485                 490                 495

His Glu Ala Leu His Asn His Tyr Thr Gln Lys Ser Leu Ser Leu Ser
            500                 505                 510

Pro Gly Lys
        515

<210> SEQ ID NO 5
<211> LENGTH: 24
<212> TYPE: DNA
<213> ORGANISM: Artificial Sequence
<220> FEATURE:
<223> OTHER INFORMATION: PCR primer for detection of IFN-gamma (sense)

<400> SEQUENCE: 5
gccatcagca acaacataag cgtc                                          24

<210> SEQ ID NO 6
<211> LENGTH: 24
<212> TYPE: DNA
<213> ORGANISM: Artificial Sequence
<220> FEATURE:
<223> OTHER INFORMATION: PCR primer for detection of IFN-gamma
      (antisense)

<400> SEQUENCE: 6
ccactcggat gagctcattg aatg                                          24
```

<210> SEQ ID NO 7
<211> LENGTH: 25
<212> TYPE: DNA
<213> ORGANISM: Artificial Sequence
<220> FEATURE:
<223> OTHER INFORMATION: PCR primer for detection of IFN-gamma R (sense)

<400> SEQUENCE: 7
gtagtaacca gtcaggccct tgtag                                  25

<210> SEQ ID NO 8
<211> LENGTH: 19
<212> TYPE: DNA
<213> ORGANISM: Artificial Sequence
<220> FEATURE:
<223> OTHER INFORMATION: PCR primer for detection of IFN-gamma R
      (antisense)

<400> SEQUENCE: 8
ccacgaggcc actgtcaga                                         19

<210> SEQ ID NO 9
<211> LENGTH: 24
<212> TYPE: DNA
<213> ORGANISM: Artificial Sequence
<220> FEATURE:
<223> OTHER INFORMATION: PCR primer for detection of IL-12R beta 2
      (sense)

<400> SEQUENCE: 9
tttccatttt tgcatcaagt tctc                                   24

<210> SEQ ID NO 10
<211> LENGTH: 25
<212> TYPE: DNA
<213> ORGANISM: Artificial Sequence
<220> FEATURE:
<223> OTHER INFORMATION: PCR primer for detection of IL-12R beta 2
      (antisense)

<400> SEQUENCE: 10
cccatcttta accgatctag agtca                                  25

<210> SEQ ID NO 11
<211> LENGTH: 20
<212> TYPE: DNA
<213> ORGANISM: Artificial Sequence
<220> FEATURE:
<223> OTHER INFORMATION: PCR primer for detection of IL-18R beta (sense)

<400> SEQUENCE: 11
tccccacagt cacatggaaa                                        20

<210> SEQ ID NO 12
<211> LENGTH: 22
<212> TYPE: DNA
<213> ORGANISM: Artificial Sequence
<220> FEATURE:
<223> OTHER INFORMATION: PCR primer for detection of IL-18R beta
      (antisense)

<400> SEQUENCE: 12
ggtaacgaat ttgggtccag aa                                     22

<210> SEQ ID NO 13
<211> LENGTH: 20
<212> TYPE: DNA

```
<213> ORGANISM: Artificial Sequence
<220> FEATURE:
<223> OTHER INFORMATION: PCR primer for detection of STAT4 (sense)

<400> SEQUENCE: 13
cacggcaggg tgaaattctc                                              20

<210> SEQ ID NO 14
<211> LENGTH: 18
<212> TYPE: DNA
<213> ORGANISM: Artificial Sequence
<220> FEATURE:
<223> OTHER INFORMATION: PCR primer for detection of STAT4 (antisense)

<400> SEQUENCE: 14
ggcaggtccc tccagtga                                                18

<210> SEQ ID NO 15
<211> LENGTH: 24
<212> TYPE: DNA
<213> ORGANISM: Artificial Sequence
<220> FEATURE:
<223> OTHER INFORMATION: PCR primer for detection of T-bet (sense)

<400> SEQUENCE: 15
ctgcctgcag tgcttctaac acac                                         24

<210> SEQ ID NO 16
<211> LENGTH: 24
<212> TYPE: DNA
<213> ORGANISM: Artificial Sequence
<220> FEATURE:
<223> OTHER INFORMATION: PCR primer for detection of T-bet (antisense)

<400> SEQUENCE: 16
acactcgtat caacagatgc gtac                                         24

<210> SEQ ID NO 17
<211> LENGTH: 24
<212> TYPE: DNA
<213> ORGANISM: Artificial Sequence
<220> FEATURE:
<223> OTHER INFORMATION: PCR primer for detection of IL-4 (sense)

<400> SEQUENCE: 17
aagaacacca cagagagtga gctc                                         24

<210> SEQ ID NO 18
<211> LENGTH: 24
<212> TYPE: DNA
<213> ORGANISM: Artificial Sequence
<220> FEATURE:
<223> OTHER INFORMATION: PCR primer for detection of IL-4 (antisense)

<400> SEQUENCE: 18
tttcagtgat gtggacttgg actc                                         24

<210> SEQ ID NO 19
<211> LENGTH: 24
<212> TYPE: DNA
<213> ORGANISM: Artificial Sequence
<220> FEATURE:
<223> OTHER INFORMATION: PCR primer for detection of IL-5 (sense)

<400> SEQUENCE: 19
caccagctat gcattggaga aatc                                         24
```

```
<210> SEQ ID NO 20
<211> LENGTH: 24
<212> TYPE: DNA
<213> ORGANISM: Artificial Sequence
<220> FEATURE:
<223> OTHER INFORMATION: PCR primer for detection of IL-5 (antisense)

<400> SEQUENCE: 20
tctgtactca tcacaccaag gaac                                            24

<210> SEQ ID NO 21
<211> LENGTH: 24
<212> TYPE: DNA
<213> ORGANISM: Artificial Sequence
<220> FEATURE:
<223> OTHER INFORMATION: PCR primer for detection of IL-10 (sense)

<400> SEQUENCE: 21
agaagcatgg ccctgaaatc aagg                                            24

<210> SEQ ID NO 22
<211> LENGTH: 24
<212> TYPE: DNA
<213> ORGANISM: Artificial Sequence
<220> FEATURE:
<223> OTHER INFORMATION: PCR primer for detection of IL-10 (antisense)

<400> SEQUENCE: 22
cttgtagaca ccttggtctt ggag                                            24

<210> SEQ ID NO 23
<211> LENGTH: 24
<212> TYPE: DNA
<213> ORGANISM: Artificial Sequence
<220> FEATURE:
<223> OTHER INFORMATION: PCR primer for detection of IL-13 (sense)

<400> SEQUENCE: 23
agcatggtat ggagtgtgga cctg                                            24

<210> SEQ ID NO 24
<211> LENGTH: 24
<212> TYPE: DNA
<213> ORGANISM: Artificial Sequence
<220> FEATURE:
<223> OTHER INFORMATION: PCR primer for detection of IL-13 (antisense)

<400> SEQUENCE: 24
cagttgcttt gtgtagctga gcag                                            24

<210> SEQ ID NO 25
<211> LENGTH: 20
<212> TYPE: DNA
<213> ORGANISM: Artificial Sequence
<220> FEATURE:
<223> OTHER INFORMATION: PCR primer for detection of STAT6 (sense)

<400> SEQUENCE: 25
tctggacacc tgctcatgca                                                 20

<210> SEQ ID NO 26
<211> LENGTH: 22
<212> TYPE: DNA
<213> ORGANISM: Artificial Sequence
<220> FEATURE:
<223> OTHER INFORMATION: PCR primer for detection of STAT6 (antisense)
```

```
<400> SEQUENCE: 26
cccagccagt tcttttctct tg                                               22

<210> SEQ ID NO 27
<211> LENGTH: 19
<212> TYPE: DNA
<213> ORGANISM: Artificial Sequence
<220> FEATURE:
<223> OTHER INFORMATION: PCR primer for detection of GATA3 (sense)

<400> SEQUENCE: 27
cagaaccggc cccttatca                                                   19

<210> SEQ ID NO 28
<211> LENGTH: 21
<212> TYPE: DNA
<213> ORGANISM: Artificial Sequence
<220> FEATURE:
<223> OTHER INFORMATION: PCR primer for detection of GATA3 (antisense)

<400> SEQUENCE: 28
cattagcgtt cctcctccag a                                                21

<210> SEQ ID NO 29
<211> LENGTH: 20
<212> TYPE: DNA
<213> ORGANISM: Artificial Sequence
<220> FEATURE:
<223> OTHER INFORMATION: PCR primer for detection of Granzyme A (sense)

<400> SEQUENCE: 29
gctggcgctt tgattgaaaa                                                  20

<210> SEQ ID NO 30
<211> LENGTH: 27
<212> TYPE: DNA
<213> ORGANISM: Artificial Sequence
<220> FEATURE:
<223> OTHER INFORMATION: PCR primer for detection of Granzyme A
      (antisense)

<400> SEQUENCE: 30
aacttagatc tctttcccac gttacag                                          27

<210> SEQ ID NO 31
<211> LENGTH: 18
<212> TYPE: DNA
<213> ORGANISM: Artificial Sequence
<220> FEATURE:
<223> OTHER INFORMATION: PCR primer for detection of Perforin 1 (sense)

<400> SEQUENCE: 31
cgtgagcgtc acgtcgaa                                                    18

<210> SEQ ID NO 32
<211> LENGTH: 21
<212> TYPE: DNA
<213> ORGANISM: Artificial Sequence
<220> FEATURE:
<223> OTHER INFORMATION: PCR primer for detection of Perforin 1
      (antisense)

<400> SEQUENCE: 32
gttcccgaag agcagatcat g                                                21

<210> SEQ ID NO 33
```

```
<211> LENGTH: 23
<212> TYPE: DNA
<213> ORGANISM: Artificial Sequence
<220> FEATURE:
<223> OTHER INFORMATION: PCR primer for detection of Klra7 (sense)

<400> SEQUENCE: 33
tctggaagat tttgggaatg ttc                                          23

<210> SEQ ID NO 34
<211> LENGTH: 23
<212> TYPE: DNA
<213> ORGANISM: Artificial Sequence
<220> FEATURE:
<223> OTHER INFORMATION: PCR primer for detection of Klra7 (antisense)

<400> SEQUENCE: 34
tgttcagtct ccacaaggaa gga                                          23

<210> SEQ ID NO 35
<211> LENGTH: 21
<212> TYPE: DNA
<213> ORGANISM: Artificial Sequence
<220> FEATURE:
<223> OTHER INFORMATION: PCR primer for detection of Klrc1 (sense)

<400> SEQUENCE: 35
acgcgtcacc tatgcagaac t                                            21

<210> SEQ ID NO 36
<211> LENGTH: 18
<212> TYPE: DNA
<213> ORGANISM: Artificial Sequence
<220> FEATURE:
<223> OTHER INFORMATION: PCR primer for detection of Klrc1 (antisense)

<400> SEQUENCE: 36
gcgaggaccc cttggttt                                                18

<210> SEQ ID NO 37
<211> LENGTH: 23
<212> TYPE: DNA
<213> ORGANISM: Artificial Sequence
<220> FEATURE:
<223> OTHER INFORMATION: PCR primer for detection of Klrd1 (sense)

<400> SEQUENCE: 37
accttctcca accaccactg tag                                          23

<210> SEQ ID NO 38
<211> LENGTH: 20
<212> TYPE: DNA
<213> ORGANISM: Artificial Sequence
<220> FEATURE:
<223> OTHER INFORMATION: PCR primer for detection of Klrd1 (antisense)

<400> SEQUENCE: 38
aacccacttg tccaggcaaa                                              20

<210> SEQ ID NO 39
<211> LENGTH: 23
<212> TYPE: DNA
<213> ORGANISM: Artificial Sequence
<220> FEATURE:
<223> OTHER INFORMATION: PCR primer for detection of Klrg1 (sense)

<400> SEQUENCE: 39
```
cagatggaag ctcaaagctg tct                                            23

<210> SEQ ID NO 40
<211> LENGTH: 19
<212> TYPE: DNA
<213> ORGANISM: Artificial Sequence
<220> FEATURE:
<223> OTHER INFORMATION: PCR primer for detection of Klrg1 (antisense)

<400> SEQUENCE: 40
ccaaagccac cattgcaaa                                                 19

<210> SEQ ID NO 41
<211> LENGTH: 19
<212> TYPE: DNA
<213> ORGANISM: Artificial Sequence
<220> FEATURE:
<223> OTHER INFORMATION: PCR primer for detection of CXCR6 (sense)

<400> SEQUENCE: 41
tttcgggctt gccttaacc                                                 19

<210> SEQ ID NO 42
<211> LENGTH: 23
<212> TYPE: DNA
<213> ORGANISM: Artificial Sequence
<220> FEATURE:
<223> OTHER INFORMATION: PCR primer for detection of CXCR6 (antisense)

<400> SEQUENCE: 42
tccagacgtt cttccagaac ttt                                            23

<210> SEQ ID NO 43
<211> LENGTH: 20
<212> TYPE: DNA
<213> ORGANISM: Artificial Sequence
<220> FEATURE:
<223> OTHER INFORMATION: PCR primer for detection of CCR4 (sense)

<400> SEQUENCE: 43
aacagagcag tgcgcatgat                                                20

<210> SEQ ID NO 44
<211> LENGTH: 19
<212> TYPE: DNA
<213> ORGANISM: Artificial Sequence
<220> FEATURE:
<223> OTHER INFORMATION: PCR primer for detection of CCR4 (antisense)

<400> SEQUENCE: 44
cgttgtacgg cgtccagaa                                                 19

<210> SEQ ID NO 45
<211> LENGTH: 17
<212> TYPE: DNA
<213> ORGANISM: Artificial Sequence
<220> FEATURE:
<223> OTHER INFORMATION: PCR primer for detection of TARC/CCL17 (sense)

<400> SEQUENCE: 45
cccgctgagg catttgg                                                   17

<210> SEQ ID NO 46
<211> LENGTH: 22
<212> TYPE: DNA
<213> ORGANISM: Artificial Sequence
<220> FEATURE:

<223> OTHER INFORMATION: PCR primer for detection of TARC/CCL17
(antisense)

<400> SEQUENCE: 46
gtcacaggcc gttttatgtt ga                                              22

<210> SEQ ID NO 47
<211> LENGTH: 20
<212> TYPE: DNA
<213> ORGANISM: Artificial Sequence
<220> FEATURE:
<223> OTHER INFORMATION: PCR primer for detection of MDC/CCL22 (sense)

<400> SEQUENCE: 47
ccctcttcaa ccgcatgcta                                                 20

<210> SEQ ID NO 48
<211> LENGTH: 22
<212> TYPE: DNA
<213> ORGANISM: Artificial Sequence
<220> FEATURE:
<223> OTHER INFORMATION: PCR primer for detection of MDC/CCL22
(antisense)

<400> SEQUENCE: 48
acacaggcaa ggagtcaaag gt                                              22

<210> SEQ ID NO 49
<211> LENGTH: 22
<212> TYPE: DNA
<213> ORGANISM: Artificial Sequence
<220> FEATURE:
<223> OTHER INFORMATION: PCR primer for detection of IL-17A (sense)

<400> SEQUENCE: 49
agcaagagat cctggtcctg aa                                              22

<210> SEQ ID NO 50
<211> LENGTH: 23
<212> TYPE: DNA
<213> ORGANISM: Artificial Sequence
<220> FEATURE:
<223> OTHER INFORMATION: PCR primer for detection of IL-17A (antisense)

<400> SEQUENCE: 50
catcttctcg accctgaaag tga                                             23

<210> SEQ ID NO 51
<211> LENGTH: 20
<212> TYPE: DNA
<213> ORGANISM: Artificial Sequence
<220> FEATURE:
<223> OTHER INFORMATION: PCR primer for detection of RORgamma t (sense)

<400> SEQUENCE: 51
ctttcaatac ctcattgtat                                                 20

<210> SEQ ID NO 52
<211> LENGTH: 20
<212> TYPE: DNA
<213> ORGANISM: Artificial Sequence
<220> FEATURE:

```
<223> OTHER INFORMATION: PCR primer for detection of RORgamma t
      (antisense)

<400> SEQUENCE: 52
aggtccttct gggggcttgc                                          20
```

METHODS FOR TREATING ALLERGIC AIRWAY INFLAMMATION, AIRWAY HYPERSENSITIVITY, AND EOSINOPHILIA

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 35,377 bytes ASCII (Text) file named "706487SequenceListing.txt," created May 26, 2010, and filed with the U.S. Patent and Trademark Office on May 27, 2010.

TECHNICAL FIELD

The present invention relates to a novel method of screening a therapeutic agent for allergic airway inflammation and/or airway hypersensitivity. More particularly, the present invention relates to a method of screening a therapeutic agent for allergic airway inflammation and/or airway hypersensitivity including measuring the Th2 cell-like function of an IL-17RB positive NKT cell, and a therapeutic agent for allergic airway inflammation and/or airway hypersensitivity, containing a substance capable of inhibiting or eliminating the Th2 cell-like function of an IL-17RB positive NKT cell as an active ingredient.

BACKGROUND ART

IL-17 is one kind of cytokine which was cloned from a T cell hybridoma of a mouse in 1993, and for which this protein was shown to have the NF-κB activating ability and the IL-6 inducing ability in 1995. IL-17 is a glycoprotein of a homodimer consisting of a peptide having a molecular weight of 20 to 30 kD, and it is currently known that it consists of six family molecules having homology (IL-17, IL-17B, IL-17C, IL-17D, IL-25(IL-17E), IL-17F) in addition to IL-17 (also referred to as IL-17A). It is known that IL-17 is produced mainly by an activated T cell (Th1 cell, Th2 cell), and acts on various cells such as fibroblast, epithelial cell, vascular endothelial cell, macrophage etc. to induce various factors such as inflammatory cytokine or chemokine, cell adhesion factor etc. to induce inflammation.

IL-17 is produced mainly from an activated T cell, while an IL-17 receptor (hereinafter, also referred to as IL-17R) is constitutively expressed in various cells. It is known that, like a ligand, a receptor forms a family (IL-17RA, IL-17RB, IL-17RC, IL-17RD, IL-17RE).

Allergic airway inflammation such as bronchial asthma etc. is evoked by interaction between a hematopoietic cell which has infiltrated into an inflammatory location, such as Th2 cell, eosinophil, neutrophil, mast cell, basophil etc. and a tissue cell such as vascular endothelial cell, epithelial cell, fibroblast etc. The Th2 cell produces Th2 cytokine/chemokine such as IL-4, IL-5, IL-13, TARC/CCL17, MDC/CCL22 etc., and plays a central role in evoking allergic airway inflammation by inducement of IgE production, activation of eosinophil, production of a mucosal fluid and other cytokine/chemokine from airway epithelial cell, and expression of an adhesion molecule on vascular endothelial cell.

In recent years, as a new Th2 cell cytokine, IL-17E/IL-25 belonging to the IL-17 family has been identified (Non-Patent Literatures 1, 2). IL-17E/IL-25 is a ligand of IL-17RB, and it is thought that it has a role of inducing production of a Th2 cytokine such as IL-4, IL-5, IL-13 etc., and causing evocation or exacerbation of airway hypersensitivity and asthma (Non-Patent Literatures 5 to 7). However, details of a Th2 cytokine producing cell which becomes a target thereof, and particularly importance of a cell having a specified subset in involvement of IL-17E/IL-25 in allergic airway inflammation and airway hypersensitivity have not been revealed yet.

It is known that a natural killer T (NKT) cell recognizes glycosphingolipid as a ligand, which has been presented to an antigen presenting molecule CD1d on an antigen presenting cell (APC), is activated, and induces production of both Th1/2 cytokines and the cytotoxic activity to cause manifestation of the function particularly important in antitumor. Since the NKT cell has the aforementioned multifunction, it involves in remission of various morbids, while cases of involvement in exacerbation have been reported. It has been reported that an activation of the NKT cell particularly triggers pathogenesis and exacerbation of asthma (Non-Patent Literatures 3, 4). In addition, in therapy of asthma, symptomatic therapy using mainly an inhaled steroid is performed, but it is known that there are steroid non-sensitive asthma patients, and it has been reported that there is correlation with cases in which the NKT cell is involved in exacerbation, in many cases (Non-Patent Literature 4).

However, it has not been known that a specified subset of the NKT cell is important in involvement in asthma.

[Non-Patent Literature 1] Lee J., et al. IL-17E, a novel proinflammatoryligand for the IL-17 receptor homolog IL-17Rh1. J Biol Chem. 2001 Jan. 12; 276(2):1660-1664.

[Non-Patent Literature 2] Fort M. M., et al. IL-25 induces IL-4, IL-5, and IL-13 and Th2-associated pathologies in vivo. Immunity. 2001 December; 15(6):985-995.

[Non-Patent Literature 3] Akbari O., et al. Essential role of NKT cells producing IL-4 and IL-13 in the development of allergen-induced airway hyperreactivity. Nat Med. 2003 May; 9(5):582-588.

[Non-Patent Literature 4] Umetsu D. T., DeKruyff R. H. A role for natural killer T cells in asthma. Nat Rev Immunol. 2006 December; 6(12):953-8.

[Non-Patent Literature 5] Angkasekwinai P., et al. Interleukin 25 promotes the initiation of proallergictype 2 responses. J Exp Med. 2007 Jul. 9; 204(7):1509-17.

[Non-Patent Literature 6] Wang Y. H., et al. IL-25 augments type 2 immune responses by enhancing the expansion and functions of TSLP-DC-activated Th2 memory cells. J Exp Med. 2007 Aug. 6; 204(8):1837-47.

[Non-Patent Literature 7] Ballantyne S. J., et al. Blocking IL-25 prevents airway hyperresponsivenessin allergic asthma. J Allergy Clin Immunol. 2007 Sep. 20.

DISCLOSURE OF THE INVENTION

Problems to be Solved by the Invention

An object of the present invention is to provide a screening method for obtaining a therapeutic agent for allergic airway inflammation and/or airway hypersensitivity, a m therapeutic agent for allergic airway inflammation and/or airway hypersensitivity having the novel action mechanism, and various means capable of developing them etc.

Means for Solving the Problems

In view of the aforementioned problems, the present inventors have intensively studied and, as a result, continued using an anti-IL-17RB monoclonal antibody that specific expression of IL-17RB is seen in a part of an unstimulated NKT cell (NKT cell in the stationary state) and, further, found out that the IL-17RB positive NKT cell becomes to exhibit the Th2 cell-like function by activation, and deeply contributes to inducement of asthma. Further, by investigating influence of the IL-17RB positive NKT cell on the Th2 cell-like function, it was found out that a method of screening a therapeutic agent for allergic airway inflammation and/or airway hypersensitivity can be carried out, resulting in completion of the present invention. That is, the present invention is as follows.

[1] A hybridoma which is a fused cell of a lymphocyte or a spleen cell isolated from a mammal, other than a human, immunized with recombinant IL-17RB in which an extracellular region of IL-17RB and a Fc region of human IgG1 are bound, and a myeloma cell strain, wherein the culture supernatant thereof specifically reacts with IL-17RB.

[2] A monoclonal antibody which is produced by the hybridoma as defined in [1], and specifically recognizes IL-17RB.

[3] A method of detecting an IL-17RB positive cell, comprising using the monoclonal antibody as defined in [2].

[4] The method according to [3], wherein the IL-17RB positive cell is an IL-17RB positive NKT cell in the stationary state.

[5] A method of separating an IL-17RB positive cell from other lymphoid cells, comprising using the monoclonal antibody as defined in [2].

[6] The method according to [5], wherein the IL-17RB positive cell is an IL-17RB positive NKT cell in the stationary state.

[7] A method of screening a therapeutic agent for allergic airway inflammation and/or airway hypersensitivity, comprising the step of measuring the Th2 cell-like function of an IL-17RB positive NKT cell.

[8] A method of screening a therapeutic agent for allergic airway inflammation and/or airway hypersensitivity, comprising the steps of:
  contacting an IL-17RB positive NKT cell with a test compound in the presence of a ligand of IL-17RB (step 1),
  measuring the Th2 cell-like function of the IL-17RB positive NKT cell contacted with the test compound and the Th2 cell-like function of an IL-17 RB positive NKT cell not being contacted with the test compound, and comparing the results (step 2), and
  selecting a test compound significantly inhibiting the Th2 cell-like function as a therapeutic agent for allergic airway inflammation and/or airway hypersensitivity (step 3).

[9] The method according to [8], wherein the Th2 cell-like function is the ligand stimulation-dependent Th2 cytokine/chemokine producing ability.

[10] The method according to [9], wherein the Th2 cytokine/chemokine is at least one kind selected from the group consisting of IL-4, IL-5, IL-13, TARC/CCL17 and MDC/CCL22.

[11] A method of screening a therapeutic agent for allergic airway inflammation and/or airway hypersensitivity, comprising the steps of:
  administering a test compound to a mammal other than a human, having an IL-17RB positive NKT cell in the presence of a ligand of IL-17RB (step 1),
  measuring the Th2 cell-like function of the mammal to which the test compound is administered, and the Th2 cell-like function of a mammal to which the test compound is not administered, and comparing the results (step 2), and
  selecting a test compound significantly inhibiting the Th2 cell-like function as a therapeutic agent for allergic airway inflammation and/or airway hypersensitivity (step 3).

[12] The method according to [11], wherein the Th2 cell-like function is ligand stimulation-dependent increase in airway resistance.

[13] The method according to any one of [8] to [12], wherein the ligand is IL-17E/IL-25.

[14] A therapeutic agent for allergic airway inflammation and/or airway hypersensitivity, containing a substance capable of inhibiting or eliminating the Th2 cell-like function of an IL-17RB positive NKT cell as an active ingredient.

[15] A therapeutic agent for eosinophilia, containing a substance capable of inhibiting or eliminating the Th2 cell-like function of an IL-17RB positive NKT cell as an active ingredient.

[16] The therapeutic agent for allergic airway inflammation and/or airway hypersensitivity according to [14], wherein the substance capable of inhibiting or eliminating the Th2 cell-like function of an IL-17RB positive NKT cell is at least one kind selected from the group consisting of an antagonistic antibody and low-molecular inhibitor to IL-17RB, an antibody to IL-17E/IL-25 and a soluble molecule of IL-17RB.

[17] The therapeutic agent for eosinophilia according to [15], wherein the substance capable of inhibiting or eliminating the Th2 cell-like function of an IL-17RB positive NKT cell is at least one kind selected from the group consisting of an antagonistic antibody and low-molecular inhibitor to IL-17RB, an antibody to IL-17E/IL-25 and a soluble molecule of IL-17RB.

Effect of the Invention

According to the present invention, an IL-17RB positive cell or an IL-17RB positive NKT cell can be selectively detected. In addition, an IL-17RB positive cell or an IL-17RB positive NKT cell can be separated from other lymphoid lineage cells selectively and at a high purity. Further, since an activated IL-17RB positive NKT cell has the Th2 cell-function from results of analysis of the function thereof and produces a large amount of a Th2 cytokine such as IL-13 etc. by stimulation of IL-17E/IL-25 serving as a ligand, it is thought that it has a central role in exacerbation of airway hypersensitivity or allergic airway inflammation. Previously, regarding an allergic disease such as asthma etc., symptomatic therapy using a steroid has been performed, but the case of steroid unresponsiveness is also known, and correlation with the case in which an NKT cell is involved in exacerbation has been pointed out. From these results, it is expected that immunological response can be controlled by inhibiting or eliminating the function of the IL-17RB positive NKT cell.

BRIEF DESCRIPTION OF THE DRAWINGS

FIG. 14a shows expression of IL-17RB in a c-kit positive non-B non-T cell of an intestinal membrane lymphatic node, FIG. 14b shows expression of IL-17RB in each subset of a spleen cell, and FIG. 14c shows expression of IL-17RB in each subset of a lung mononuclear cell.

FIG. 22a is a view of confirmation that an IL-17RB positive NKT cell has been eliminated, and FIG. 22b is a view showing the measurement results of an airway resistance value.

FIG. 27a shows the results of investigation of increase in an airway resistance value by ligand administration. FIG. 27b shows the results of investigation of cell infiltration into an alveolus fluid by ligand administration.

FIG. 28a shows the results of investigation of infiltration of eosinophil/neutrophil into an alveolus fluid by ligand administration, and FIG. 28b shows the results of investigation of mucin overproduction by ligand administration.

BEST MODE FOR CARRYING OUT THE INVENTION

Figure 1:
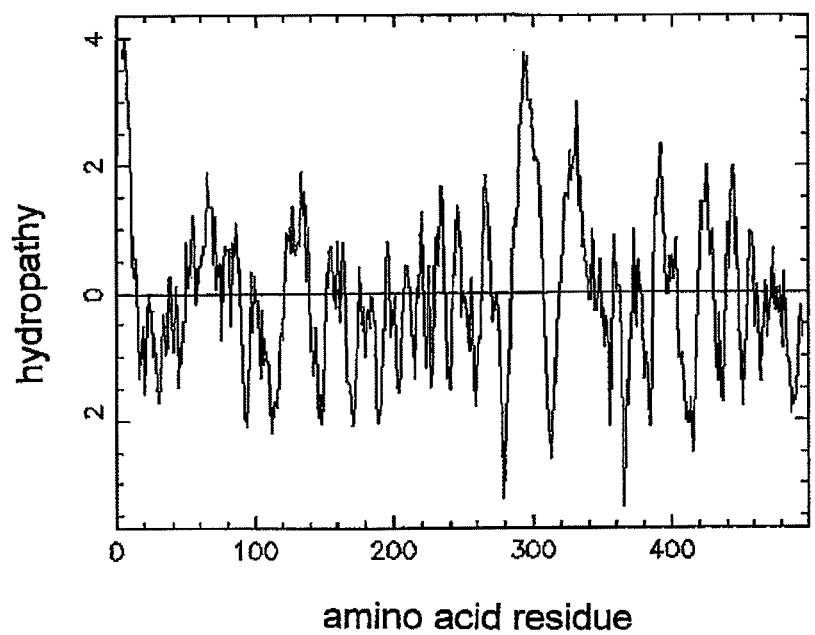
FIG. 1 is a view showing the results of hydropathy plot analysis of IL-17RB.

Unless otherwise is indicated in sentences, all technical terms and scientific terms used herein have the same meanings as those that are generally understood by a person skilled in the technical field to which the present invention belongs. Arbitrary methods and materials which are same as or equivalent to those described in the present specification can be used in implementation or tests of the present invention, and preferable methods and materials are described below. All publications and patents referred in the present specification are incorporated herein by reference, for the purpose of describing and disclosing the constructs and methodologies, described in the publications which are usable with reference to the described inventions.

An antibody to IL-17RB and a monoclonal antibody which specifically recognizes IL-17RB of the present invention used in the present specification (hereinafter, both are collectively also referred to as the antibody of the present invention for convenience) mean that the antibody of the present invention immunologically cross-reacts with an epitope possessed only by an IL-17RB molecule, and does not cross-reacts with other family protein. Such epitope can be determined by selecting an essentially different sequence part (continuous at least 5 amino acids, preferably at least 8 amino acids, further preferably at least 15 amino acids) by aligning and comparing, for example, an amino acid sequence of IL-17RB and an amino acid sequence of other protein.

An antigenic epitope for obtaining an objective antibody can be selected from a region having high antigenecity, a region having superficiality, a region having a possibility of not taking a secondary structure, and a region having no or low homology with other protein (particularly, other protein of a family to which IL-17RB belongs), in an amino acid sequence of IL-17RB (a presumed amino acid sequence is shown in SEQ ID No.: 2, and a base sequence is shown in SEQ ID No.: 1). Herein, the term "homology" means identity or similarity of sequences between two or more amino acid sequences or base sequences, and sequences can be compared by the conventional methods including, for example, a diagonal line diagram method and a frequency distribution method. The region having high antigenecity can be presumed by the method of Parker et al. [Biochemistry, vol. 25, pp. 5425-5432 (1986)]. The region having superficiality can be presumed, for example, by calculating and plotting a hydropathy index. The region having a possibility of not taking a secondary structure can be presumed, for example, by the method of Chou and Fasman [Adv. Enzymol. Relat. Areas Mol. Biol., vol. 47, pp. 45-148(1978)]. Further, the region having no or low homology with particularly other protein to which IL-17RB belongs can be presumed by comparing homology between an amino acid sequence of IL-17RB and an amino acid sequence of other protein.

Based on a partial amino acid sequence of IL-17RB capable of functioning as an antigenic epitope presumed by the aforementioned procedure, a peptide consisting of the amino acid sequence can be synthesized by utilizing a peptide synthesis method. An objective peptide is synthesized using, for example, a commercially available peptide synthesizer based on solid phase peptide synthesis developed by R. B. Merrifield [Science, vol. 232, pp. 341-347(1986)], a protective group is deprotected thereof, and the obtained peptide is then purified by one or combination of methods of an ion exchange chromatography, gel filtration chromatography, and reverse phase chromatography etc. The resulting purified peptide is bound with a carrier protein such as keyhole limpet hemocyanin (KLH) and albumin, and can be used as an immunogen.

Further, a polyclonal antibody or a monoclonal antibody to IL-17RB can be made by the known procedure using gene recombinant IL-17RB (hereinafter, also referred to as recombinant IL-17RB for convenience) as an immunogen. In this case, the term "recombinant" used regarding IL-17RB, a monoclonal antibody, a polyclonal antibody, or other protein means that these proteins were produced by a recombinant DNA in a host cell. The recombinant may encode the aforementioned antigenic epitope part for obtaining an objective antibody, that is, a partial amino acid sequence of IL-17RB, or may encode a full length amino acid sequence or an arbitrary partial amino acid sequence of IL-17RB, as far as it contains the sequence. The recombinant DNA can be used by inserting into a suitable vector. A kind of the vector used in the present invention is not particularly limited, but may be, for example, an autonomously replicating vector (e.g. plasmid etc.), or the vector may be integrated into a genome of a host cell upon introduction into the host cell, and replicated with a chromosome in which the vector has been incorporated.

Preferably, the vector used in the present invention is an expression vector. In the expression vector, a gene encoding recombinant IL-17RB is functionally connected to a suitable transcription/tranlation regulating sequence (e.g. promoter etc.). Examples of a kind of the expression vector include a plasmid, a phage, a cosmid, a virus etc. The promoter is a DNA sequence exhibiting the transcription activity in a host cell, and can be arbitrarily selected depending on a kind of a host.

A promoter and an enhancer selected depending on a host/vector system used can be contained in the transcription/translation regulating sequence. Alternatively, the aforementioned recombinant DNA may be functionally connected to a suitable terminator, if necessary. Furthermore, the recombinant vector may further have an element such as polyadenylation signal (e.g. derived from SV40 or an adenovirus 5E1b region), a transcription enhancer sequence (e.g. SV40 enhancer) etc. Further, a selection marker gene for selection of a transformed cell (a gene imparting resistance to drug such as tetracycline, ampicillin, kanamycin, hygromycin, phosphinothricin etc., gene for supplementing an auxotrophy mutation etc) may be further contained.

By introducing the recombinant DNA or the recombinant vector into a suitable host, a transformant expressing recombinant IL-17RB can be made. As a host cell into which a DNA or a vector is introduced, an arbitrary cell can be used as far as it can express recombinant IL-17RB. As a host cell, a prokaryotic cell, yeasts, an animal cell, a fungal cell, an insect cell or a plant cell can be used.

Transformation of the prokaryotic cell can be performed using a competent cell by a protoplast method, or the known method. Examples of a method of introducing a vector into a yeast host include an electroporation method, a spheroplast method, a lithium acetate method etc. As a method of introducing a vector into an animal cell, for example, an electroporation method, a calcium phosphate method, a lipofection method etc. can be used. When a flamentous bacterium is used as a host cell, transformation can be performed by incorporating a DNA construct into a host chromosome to obtain a recombinant host cell. Incorporation of the DNA construct into a host chromosome can be performed, for example, by homologous recombination or heterogeneous recombination according to the known method. When an insect cell is used as a host, a recombinant gene introduction vector and baculovirus are co-introduced into an insect cell to obtain a recombinant virus in the insect cell culturing supernatant and, further, the recombinant virus is made to infect an insect cell, thereby, a protein can be expressed.

A transformed or transfected host cell is cultured in a suitable culturing medium to express an objective gene, and produced recombinant IL-17RB is recovered from the medium or the host cell. In case of the recovery from a cell, after completion of culturing, a cell is separated by centrifugation etc., suspended in an aqueous buffer, and the cell is crushed by ultrasound treatment, a French press, a dinomill etc. to obtain a cell-free extract. Isolation and purification of a membrane molecule can be performed by arbitrarily combining the general methods used in purification of a protein, for example, a gel filtration, chromatography such as ion exchange chromatography, affinity chromatography, and hydrophobic chromatography etc, HPLC, electrophoretic method, desalting method, organic solvent precipitation method etc.

The "antibody" of the present invention may be any of a peptide antibody, polyclonal antibody, and monoclonal antibody. The "antibody" is obtained by immunizing a mouse or other suitable animal with an antigen or an antigen expressing cell by a subcutaneous, intraperitoneal or intramuscular route, in order to induce a lymphocyte or a spleen cell which produces or would produce an antibody probably specifically binding to a protein used in immunization. Examples of the antigen include the antigenic epitope for obtaining the above objective antigen, and a partial amino acid sequence comprising the epitope, and examples of the antigen expressing cell include a host cell transformed or transfected with a recombinant DNA encoding the antigenic epitope for obtaining the above objective antigen or a partial amino acid sequence comprising the epitope. Further, an antigen or an antigen expressing cell is administered to a transgenic animal having a repertory of a human antibody gene as a host animal, whereby a desired human antibody may be obtained [see Proc. Natl. Acad. Sci. USA, vol. 97, pp. 722-727 (2000), International Publication WO 96/33735, WO 97/07671, WO 97/13852, WO98/37757]. Instead, a lymphocyte may be immunized in vitro. By colleting fractions binding to an antigen from serum obtained from a host animal, and purifying them, a polyclonal antibody can be obtained. In addition, for forming a hybridoma cell, a lymphocyte or a spleen cell is fused with a myeloma cell strain using a suitable fusing reagent such as polyethylene glycol, whereby a monoclonal antibody can be made (Goding, Monoclonal Antibodies: Principals and Practice pp. 59-103, Academic Press, 1986). For example, the monoclonal antibody of the present invention can be made by using a hybridoma method [Nature, vol. 256, pp. 495 (1975)], or using a recombinant DNA method (Cabilly et al., U.S. Pat. No. 4,816,567).

The antigenic protein can be prepared by expressing a DNA encoding a whole or partial sequence of a protein of IL-17RB in *Escherichia coli*, yeast, an insect cell, an animal cell etc. The resulting antigenic protein is purified by one or combination of methods of affinity chromatography, ion exchange chromatography, gel filtration chromatography, reverse phase chromatography etc, and this purified authentic product is used as an immunogen.

In addition, the antigen of present invention may be an intact antibody, or an antigen fragment such as (Fab')$_2$ and Fab, or a recombinant antibody such as a single strand antibody etc.

In addition, a chimeric antibody in which a constant region is substituted with a human constant region (e.g. mouse-human chimeric antibody: Cabilly et al., U.S. Pat. No. 4,816,567 and Morrison et al., Proc. Natl. Acad. Sci. USA, vol. 89, pp. 6851(1984)), and a humanized antibody in which a constant region, and a whole variable region except for a supervariable region (or Complementary-determining region; CDR) are substituted with human sequences (Carter et al., Proc. Natl. Acad. Sci. USA, vol. 89, pp. 4285, 1992 and Carter et al., BioTechnology, vol. 10, pp. 163, 1992) are also included in the antibody of the present invention.

For example, a recombinant in which a region thought to be an extracellular domain of IL-17RB (e.g. amino acid position 1 to position 282 of SEQ ID No.: 2) and an Fc region of human IgG1 are bound can be used as an immunogen. An amino acid sequence of the recombinant is shown in SEQ ID No.: 4. In the recombinant used in the present invention, amino acid replacements at three positions were performed so that an Fcγ receptor present on a cell surface is not bound (302 position (Leu→Ala), 303 position (Leu→Glu), 469 position (Val→Asp) in an amino acid sequence shown in SEQ ID No.: 4).

In addition, an antibody to the thus obtained antibody of the present invention, that is, an anti-idiotype antibody is also included in the present invention.

The thus obtained various antibodies to IL-17RB can be used in a variety of intended uses utilizing the characteristics thereof. The present antibody is labeled with a fluorescent substance (rhodamine, fluorescamine etc.), and a cell expressing objective IL-17 RB (IL-17RB positive cell), particularly, an IL-17RB positive NKT cell can be detected and separated using the well-known FACS. Further, an existence manner of an IL-17RB positive NKT cell in various organs can be known. Alternatively, the IL-17RB positive NKT cell can be similarly detected and separated by labeling with biotin, using avidin with phycoerythrin etc. bound thereto. Herein, the separation means separation from other cells, particularly lymphoid lineage cells, specifically, a B cell, a T cell, macrophage, a dendritic cell, an NK cell and an IL-17RB negative NKT cell, polymorphonuclear leukocyte such as neutrophil, eosinophil, basophil etc., an immunocyte such as mast cell etc.

Detection of IL-17RB is not limited to detection with FACS. For example, it is predicted that IL-17RB can be detected by acting the present antibody as a 1st antibody in Western blotting, and expression at a protein level can be confirmed. Alternatively, the present antibody is bound to a solid phase (polystyrene beads, microtiter well surface, latex beads etc.), an immunological reaction is performed in a heterogeneous system or a homogeneous system, and IL-17RB can be detected and quantitated (using a method such as a fluorescent antibody method, ELISA, radioimmunoassay etc.). In this case, the immunological reaction may be a competition reaction or a non-competition reaction. Alternatively, a reaction by a sandwich method using two or more antibodies (monoclone or polyclone) may be used. For the detection and the quantitation, any immunological procedure known in the art can be used.

Activation by stimulation of an IL-17RB ligand in an IL-17RB positive NKT cell to induce the Th2 cell-like function is the finding obtained in the present invention.

In the present invention, examples of the IL-17RB positive cell include an activated Th2 cell, an activated eosinophil etc. In addition, in the stationary state, examples of the IL-17RB positive cell preferably include an IL-17RB positive NKT cell. The IL-17RB positive NKT cell is seen, particularly, in a CD4 positive NKT cell among the NKT cell, and accounts for about ⅓ among the CD4 positive NKT cell. The cell is often seen in spleen, thymus, and lung. Herein, the "stationary state" indicates the state wherein a living body is in the healthy state, and has no allergic disease such as, particularly, asthma and ulcerous colitis.

The present invention provides a method of screening a therapeutic agent for allergic airway inflammation and/or airway hypersensitivity, comprising measuring the Th2 cell-like function of an IL-17RB positive NKT cell, particularly, an IL-17RB positive NKT cell activated by ligand stimulation. The allergic airway inflammation is inflammation in an airway generated by inhaling an allergen (e.g. environmental antigen such as mite and house dust) to cause an immunological reaction in a bronchial mucosa, releasing histamine, leukotriene, and a chemical transmitter, and inducing an allergic inflammation reaction by mast cell, eosinophil, neutrophil, and lymphocyte, and is accompanied with asthma attack in some cases. In airway hypersensitivity, a throat is constricted by responding to non-specific various stimulations, and is accompanied with asthma attack. By slight stimulation, a throat excessively reacts and, even when the cool air is inhaled, or one runs abruptly, asthma attack is caused in some cases.

In the present invention, the "Th2 cell-like function" means the function equivalent to that of helper T cell type 2 (Th2 cell) which produces a cytokine such as IL-4, IL-5, IL-6, IL-10, IL-13 etc. which control humoral immunity, and promotes production of an antibody by a B cell. Specifically, the function means the ability that an activated IL-17RB positive NKT cell produces cytokine/chemokine such as IL-4, IL-5, IL-13, TARC/CCL17, MDC/CCL22 etc., and various actions that produced various cytokines/chemokines can exert.

Further, the IL-17RB positive NKT cell activated by ligand stimulation has the function of producing eosinophil chemotactic factor (ECF-L) and mobilizing IL-5 producing eosinopohil to a location.

IL-4 (interleukin-4) is one kind of cytokine which is produced from an activated CD4 positive T cell (Th2 cell), a CD8 positive T cell, a mast cell (labrocyte), basophil, or an NKT cell, promotes proliferation and differentiation of the Th2 cell, acts on an activated B cell to promote class switch from IgM to IgG1 and IgE, and promotes production of an IgG1 antibody or an IgE antibody. In addition, it is known that IL-4 inhibits activation of macrophage, and inhibits production of NO, prostaglandin (PGE$_2$), and IFN-γ.

IL-5(interleukin-5) is a cytokine which is mainly produced by an activated T cell and a mast cell, and plays an important role in activation, proliferation and differentiation of a B cell and eosinophil. In addition, production promotion of a cytotoxic T cell in the presene of IL-2, and the histamine release potentiating action of basophil have been revealed. There are many reports suggesting a relationship between an allergic disease such as allergic rhinitis, asthma, and atopic dermatitis and IL-5.

It has been reported that IL-13 (interleukin-13) acts as an effector molecule of asthma and, for example, just administration of IL-13 to a non-sensitive animal manifests symptom characteristic in allergic asthma such as airway hypersensitivity, eosinophilic inflammation, and mucosal dysplasia.

Both of TARC/CCL17 and MDC/CCL22 are a specific ligand of CCR4, and are a chemokine expressed in a Th2 cell.

Therefore, examples of measurement of the Th2 cell-like function of an IL-17RB positive NKT cell include measurement of the ability to produce ligand stimulation-dependent Th2 cytokine/chemokine (IL-4, IL-5, IL-13, TARC/CCL17, MDC/CCL22 etc.), measurement of the presence or the absence of ligand stimulation-dependent increase in an airway resistance (in vivo measurement), measurement of the number of immunocytes, particularly, eosinophils contained in an alveolus washing solution accompanied with them, etc. Detailed measurement methods/measurement procedures will be described later.

The IL-17RB positive NKT cell used in the present screening method can be obtained by detecting and separating an NKT cell expressing IL-17RB from a cell population containing an NKT cell using the antibody of the present invention. The NKT cell is one kind of lymphocyte which is small in its existence ratio, but has a controlling role in immune system. The NKT cell has two antigen receptors of a T cell receptor (TCR) and an NK receptor. An origin of the NKT cell is not particularly limited, but the NKT cell can be recovered from umbilical blood, peripheral blood, lung, bone marrow, spleen, lymph node, thymus gland etc. of a mammal such as a primate including human, a rodent, rabbit, cat, dog, horse, cow, sheep, goat, and pig. A term "primate" used herein means an arbitrary animal belonging to a group of a mammal, which is not limited to, but includes monkey, ape and human. Specifically, a suspension of a single cell recovered from a homogenate of peripheral blood, lung, spleen or thymus gland is selected and recovered by FACS analysis using an antigenic glycolipid such as α-galactosyl ceramide bound with a CD1d molecule (α-GalCer or α-GC), which can be recognized by TCR highly retained in the NKT cell, and then only the NKT cell expressing IL-17RB is selected and recovered using the aforementioned antibody to IL-17RB (preferably, monoclonal antibody). Alternatively, since IL-17RB is specifically expressed in a part of the NKT cell in the stationary state, an IL-17RB positive NKT cell can be also selected and recovered from a suspension of a single cell recovered from a homogenate of peripheral blood, lung, spleen, or thymus gland, preferably direct from a leukocyte derived from spleen using an antibody to IL-17RB (preferably, monoclonal antibody).

One aspect (aspect 1) of a method of screening a therapeutic agent for allergic airway inflammation and/or airway hypersensitivity of the present invention will be shown below.

Aspect 1

(Step 1) A step of contacting an IL-17RB positive NKT cell with a test compound in the presence of a ligand of IL-17RB.

Examples of the IL-17RB positive NKT cell used in the present step include aforementioned cells which were detected and separated with the antibody to IL-17RB (preferably, monoclonal antibody). The NKT cell is preferably activated by APC, or is used in the condition under which the cell is activated. Specifically, the present step is performed in the presence of APC. A ligand used in the present step is not particularly limited as far as it is a substance which acts on the IL-17RB positive NKT cell to induce the Th2 cell-like function, that is, produces a Th2 cytokine or chemokine, but it is preferable to use IL-17E/IL-25 known as a ligand of IL-17RB. A concentration of the ligand used is arbitrarily set in such a range that the ligand does not disadvantageously act on proliferation of the IL-17RB positive NKT cell, preferably the ligand can promote proliferation to produce a Th2 cytokine or chemokine, and is usually 0.1 to 10 ng/ml, preferably around 1 ng/ml in a culturing solution or a buffer which becomes a medium of a reaction system. Herein, the ligand may be added to the reaction system before contact of a test compound with the IL-17RB positive NKT cell, or may be added to the reaction system after contact, or may be added to a reaction system simultaneously with the contact, as far as the ligand is present in the reaction system in the state where it acts on the IL-17RB positive NKT cell to produce a Th2 cytokine or chemokine.

In the present specification, the "test compound" is a compound which was selected or synthesized for the purpose of investigating whether it can act on the IL-17RB positive NKT cell to inhibit or eliminate the function thereof or not, and also includes the known compound which has already been reported to have other action, in addition to a novel compound. Alternatively, the test compound may be used as a composition. Examples include a nucleic acid (e.g. nucleoside, oligonucleotide, polynucleotide), a carbohydrate (e.g. monosaccharide, disaccharide, oligosaccharide, polysaccharide), a lipid (e.g. saturated or unsaturated straight, branched and/or ring-containing fatty acid), an amino acid, a protein (e.g. oligopeptide, polypeptide), an organic low-molecular compound, a compound library made using the combinatorial chemistry technique, a random peptide library made by solid phase synthesis or a phage display method, a natural component (e.g. compounds derived from microorganism, animal and plant, marine organism etc.), food, drinkable water etc. A compound which was recognized to have the action of inhibiting or eliminating the function of the IL-17RB positive NKT cell by the screening method of the present, invention is expected to apply to allergic airway inflammation or airway hypersensitivity as described above.

A method of contacting the IL-17RB positive NKT cell with the test compound is not particularly limited, as far as whether the test compound influences the ability to produce Th2 cytokine/chemokine possessed by an activated IL-17RB positive NKT cell or not can be determined, but the contact is simply performed by adding a predetermined amount in the presence of a ligand, in a reaction system such as a cell suspension containing an IL-17RB positive NKT cell and its activating substance (e.g. ligand and antigen presenting cell). An additional amount of the test compound is arbitrarily set depending on the situation of the cell, and usually it is preferable to set a dilution series. A period of time required for the contact can be arbitrarily set in such a range that the desired effect is obtained, and is usually 24 to 120 hours, preferably around 48 to 72 hours.

(Step 2) A step of measuring the Th2 cell-like function of the IL-17RB positive NKT cell contacted with the test compound and the Th2 cell-like function of an IL-17RB positive NKT cell not being contacted with the test compound, and comparing the results.

It is preferable that the IL-17RB positive NKT cell has been activated by an antigen presenting cell (APC) etc. By stimulating such the IL-17RB positive NKT cell with a ligand of IL-17RB (e.g. IL-17E/IL-25), the Th2 cell-like function is induced. Examples of the Th2 cell-like function specifically include the ability to produce Th2 cytokine/chemokine. Examples of the Th2 cytokine/chemokine include IL-13, IL-4, TARC/CCL17, MDC/CCL22 etc. as described above. The ability to produce these cytokines/chemokines can be usually measured by the method which is performed in the art, for example, Western blotting and an ELISA method using an antibody to each cytokine/chemokine, Northern blotting using a probe, and quantitative PCR using a primer. Various antibodies, probes and primers can be arbitrarily prepared based on an amino acid sequence or a gene sequence of each cytokine/chemokine, or the known information such as a purification method etc., or are commercially available.

(Step 3) A step of selecting a test compound significantly inhibiting the Th2 cell-like function as a therapeutic agent for allergic airway inflammation and/or airway hypersensitivity.

As in the Step 2, examples of the Th2 cell-like function include the ability to produce the Th2 cytokine/chemokine. It is thought that the Th2 cytokine/chemokine produced by the IL-17RB positive NKT cell has a central role in exacerbation of airway hypersensitivity or asthma, and therefore a test compound significantly inhibited the Th2 cell-like function, particularly inhibited production of the Th2 cytokine/chemokine, and selected based on the information obtained in the Step 2 can be a candidate of a therapeutic agent for allergic airway inflammation and/or airway hypersensitivity. Significance of the effect can be usually determined by performing a significance test based on statistical treatment carried out in the art.

Further, another aspect (aspect 2) of the screening method provided by the present invention will be indicated below.

Aspect 2

(Step 1) A step of administering the test compound to a mammal other than a human having an IL-17RB positive NKT cell in the presence of a ligand of IL-17RB (Step 1).

A mammal other than a human having the IL-17RB positive NKT cell used in the present step is not particularly limited as far as it is a mammal other than a human, for which the action such as IL-17RB ligand stimulation-dependent production of Th2 cytokine/chemokine and increase in an airway resistance etc. is recognized, and the examples thereof include a mammal such as a primate other than a human, a rodent, rabbit, cat, dog, horse, cow, sheep, goat, and pig. Among the examples, it is particularly desirable to be Th2 predominant. For example, in the case of mouse, Balb/c or DBA/2cr lineage mouse known to be Th2 predominant is more preferably used than C57BL/6 or C3H/HeN lineage known to be Th1 predominant (see Example 4). Examples of the ligand of IL-17RB and the test compound include the same ligand and test compound as those used in the aspect 1 of the screening method of the present invention.

A dose of the ligand of IL-17RB is not particularly limited as far as it is such an amount as to induce the Th2 cell-like function ligand stimulation-dependently, for an IL-17RB positive NKT cell (preferably, in the activated state) present in a body of a mammal other than a human, that is, as to produce Th2 cytokine/chemokine (IL-13, IL-4, TARC/CCL17, MDC/CCL22 etc.), and/or as to lead to increase in an airway resistance by an airway constricting substance (methacholine etc.) stimulation, and is usually 1 to 100 mg, preferably around 1 to 10 mg per 1 kg weight. An order of administering the test compound and the ligand to a mammal other than a human is not particularly limited as far as the Th2 cell-like function of the IL-17RB positive NKT cell is induced, and influence of the test compound on the function can be measured, and administration of the test compound may be before administration of the ligand, or after administration of the ligand. In addition, timing for arbitrary administration can be studied, depending on an action point which is desired as a therapeutic agent for allergic airway inflammation and/or airway hypersensitivity, particularly a therapeutic agent for asthma.

(Step 2) A step of measuring the Th2 cell-like function of the mammal to which the test compound is administered and a mammal to which a test compound is not administered, and comparing the results.

In the present step, examples of the "Th2 cell-like function" include the same functions as those described in the aspect 1 of the screening method of the present invention. Specifically, the examples include measurement of the ability to produce ligand stimulation-dependent Th2 cytokine/chemokine (IL-4, IL-5, IL-13, TARC/CCL17, MDC/CCL22 etc.), measurement of the presence or the absence of ligand stimulation-dependent increase in an airway resistance, measurement of the number of immunocytes (particularly, eosinophil) contained in an alveolus washing solution accompanied with this, etc. Measurement of the ability to produce ligand stimulation-dependent Th2 cytokine/chemokine is carried out by the same method as that described in the aspect 1 of the screening method of the present invention. The presence or the absence of ligand stimulation-dependent increase in an airway resistance can be measured using an ovalbumin (OVA)-inducing airway inflammation model (asthma model). The airway inflammation model using OVA is such that, after immunization with OVA-alum, OVA is inhaled to cause airway inflammation. Since the object of the present invention is to measure the Th2 cell-like function of the IL-17RB positive NKT cell using this model, ligand of IL-17RB is used for inducing the Th2 cell-like function of the IL-17RB positive NKT cell. By the inducement, eosinophilic infiltration is recognized at a periphery of bronchus or at a periphery of a blood vessel. When airway constriction is caused by methacholine etc., there is a very strong reaction, and an airway resistance is increased. The Th2 cell-like function of the IL-17RB positive NKT cell is measured based on an extent of this increase in an airway resistance. By measuring whether the test compound inhibits this increase in the airway resistance or not, usefulness of the test compound as a therapeutic agent for allergic airway inflammation and/or airway hypersensitivity can be confirmed. Measurement of the number of immunocytes (particularly, eosinophil) contained in the alveolus washing solution can be usually performed using the method usually performed in the field of a clinical test. For example, the eosinophil can be distinguished by a Giemsa staining method, and the number of the eosinophils in the alveolus washing solution can be measured. Alternatively, by paying an attention to CCR3 which is an eosinophil-specific surface molecule, the number of the eosinophils can be measured by counting CCR3 positive cells. By measuring whether the test compound inhibits, for example, increase in the number of he eosinophils in the alveolus washing solution or not, usefulness of the test compound as a therapeutic agent for allergic airway inflammation and/or airway hypersensitivity can be confirmed.

(Step 3) A step of selecting a test compound significantly inhibiting the Th2 cell-like function as a therapeutic agent for allergic airway inflammation and/or airway hypersensitivity.

The present step can be performed as in the step 3 of the aspect 1 of the screening method of the present invention.

In the screening method of the present invention, preferably, a positive control compound can be used. The positive control compound is a compound known to inhibit the Th2 cell-like function of the IL-17RB positive NKT cell, that is, the ability to produce Th2 cytokine or chemokine by stimulation with the ligand, in advance. Specifically, examples include an antagonistic antibody and a low-molecular inhibitor to IL-17RB, an antibody to IL-17E/IL-25, and a soluble molecule of IL-17RB.

The antagonistic antibody to IL-17RB inhibits or eliminates the function of the IL-17RB positive NKT cell by antagonistically acting on IL-17RB which is a target antigen, or inhibiting binding of IL-17RB and a ligand thereof, and the antibody to IL-17E/IL-25 inhibits or eliminates the function by inhibiting binding of IL-17RB and a ligand thereof. Examples of the low-molecular inhibitor to IL-17RB include a low-molecular substance capable of regulating interaction between IL-17RB and a ligand thereof to inhibit or eliminate the Th2 cell-like function of the IL-17RB positive NKT cell, and a low-molecular substance capable of regulating an intracellular signal pathway regarding IL-17RB and a ligand thereof to inhibit or eliminate the Th2 cell-like function of the IL-17RB positive NKT cell. Further, a soluble molecule of IL-17RB (i.e. a molecule corresponding to an extracellular region) inhibits or eliminates the function of the IL-17RB positive NKT cell, by competitively binding to the ligand. A used concentration of the positive control compound is not particularly limited, as far as it is such a concentration that the action of inhibiting or eliminating the function of the IL-17RB positive NKT cell is confirmed, but the concentration is different depending on a kind of a compound used and, for example, in the case of using the antagonistic antibody to IL-17RB, the concentration is usually 1 to 100 mg, preferably around 1 to 10 mg per 1 kg weight.

As the antagonistic antibody and the low-molecular inhibitor to IL-17RB, the antibody to IL-17E/IL-25, and the soluble molecule of IL-17RB, the same substances as those that can inhibit or eliminate the Th2 cell-like function of the IL-17RB positive NKT cell, contained in a therapeutic agent for allergic airway inflammation and/or airway hypersensitivity described later are used, respectively.

The present invention also provides a therapeutic agent for allergic airway inflammation and/or airway hypersensitivity, containing a substance inhibiting or eliminating the Th2 cell-like function of an IL-17RB positive NKT cell as an active ingredient. Examples of the substance inhibiting or eliminating the Th2 cell-like function of the IL-17RB positive NKT cell include an antagonistic antibody and a low-molecular inhibitor to IL-17RB, an antibody to IL-17E/IL-25, and a soluble molecule of IL-17RB. Further, examples include such a substance that inhibits expression of IL-17RB in the NKT cell, for example, an antisense nucleic acid (e.g. a DNA, an RNA, or a modified nucleotide, or a chimeric molecule thereof), a ribozyme, an RNAi-inducing nucleic acid (a polynucleotide capable of inducing the RNAi effect by introduction into a cell, preferably RNA: e.g. siRNA), an aptamer, and an expression vector comprising a nucleic acid encoding them.

Examples of the antagonistic antibody to IL-17RB include antibodies which antagonistically act on IL-17RB, among the aforementioned antibodies used for detecting and separating the IL-17RB positive NKT cell. Confirmation of the action can be performed by investigating an influence of the IL-17RB positive NKT cell induced by ligand stimulation, on the Th2 cell-like function. As the low-molecular inhibitor, a low-molecular inhibitor screened by using an IL-17RB forcibly expressing cell (e.g. IL-17RB forcibly expressing 293T cell), or measuring binding property to a soluble recombinant can be used. The antibody to IL-17E/IL-25 used in the present invention can be prepared as a polyclonal antibody or a monoclonal antibody thereof, by the well-known immunological procedure, as in the antibody to IL-17RB. Alternatively, the antibody may be a fragment of an antibody (e.g. Fab, F(ab')$_2$), or a recombinant antibody (e.g. single strand antibody). As the substance capable of inhibiting or eliminating the Th2 cell-function of the IL-17RB positive NKT cell, an IL-17RB soluble molecule can be used. The IL-17RB soluble molecule is a protein molecule containing a partial amino acid sequence including an extracellular region of IL-17RB, and specifically has a position 1 to position 282 amino acid sequence in SEQ ID No.: 2.

When the substance capable of inhibiting or eliminating the Th2 cell-like function of the IL-17RB positive NKT cell, which is an active component, is a nucleic acid molecule or a protein molecule, the therapeutic agent of the present invention can also contain an expression vector comprising the nucleic acid molecule or a nucleic acid molecule encoding the protein molecule as an active component. The expression vector must be such that an oligonucleotide or a polynucleotide encoding the nucleic acid molecule is functionally connected to a promoter capable of exerting the promoter activity in a cell of a mammal to which the expression vector is administered. The promoter which can be contained in the expression vector of the present invention is not particularly limited, as far as it enables expression of a factor under its control, but is arbitrarily selected depending on a kind of the factor, and examples thereof include a polIII promoter (e.g. tRNA promoter, U6 promoter, H1 promoter), and a promoter for a mammal (e.g. CMV promoter, CAG promoter, SV40 promoter). Alternatively, as the promoter to be used, a promoter specific for a lymphocyte (e.g. lck promoter, Pmed1 promoter) may be used.

The expression vector preferably contains a transcription termination signal, that is, a terminator region downstream of an oligo(poly)nucleotide encoding a nucleic acid molecule. Further, the expression vector can further contain a selection marker gene for selecting a transformed cell (a gene which imparts resistance to a drug such as tetracycline, ampicillin, kanamycin, hygromycin, phosphinothricin etc., gene for supplementing an auxotrophy mutation etc.)

A vector of a fundamental skeleton used as the expression vector may be a plasmid or a virus vector, and examples of a vector suitable for administration to a mammal such as a human etc. include virus vectors such as adenovirus, retrovirus, adeno-associated virus, herpesvirus, vaccinia virus, poxvirus, poliovirus, sindbis virus, sendai virus etc.

The therapeutic agent of the present invention can contain an arbitrary carrier, for example, a pharmaceutically acceptable carrier, in addition to the substance capable of inhibiting or eliminating the Th2 cell-like function of the IL-17RB positive NKT cell. Examples of the pharmaceutically acceptable carrier are not limited to, but include excipients such as sucrose, starch, mannit, sorbit, lactose, glucose, cellulose, talc, calcium phosphate, calcium carbonate etc., binders such as cellulose, methylcellulose, hydroxypropylcellulose, polypropylpyrrolidone, gelatin, gum arabic, polyethylene glycol, sucrose, starch etc., disintegrating agents such as starch, carboxymethylcellulose, hydroxypropylstarch, sodium-glycol-starch, sodium bicarbonate, calcium phosphate, calcium citrate, etc., lubricants such as magnesium stearate, aerosil, talc, sodium laurylsulfate etc., aromatic substances such as citric acid, menthol, glycyrrhizin.ammonium salt, glycine, orange powder etc., preservatives such as sodium benzoate, sodium hydrogen sulfide, methylparaben, propylparaben etc., stabilizers such as citric acid, sodium citrate, acetic acid etc., suspending agents such as methylcellulose, polyvinylpyrrolidone, aluminum stearate etc., dispersants such as surfactant etc., diluents such as water, physiological saline, orange juice etc., base waxes such as cacao butter, polyethylene glycol, kerosene etc.

Preparations suitable for oral administration are liquid preparations in which an effective amount of a substance is dissolved in a diluting solution such as water and physiological saline, capsules, saches or tablets containing an effective amounts of a substance as a solid or a granule, suspensions in which an effective amount of a substance is suspended in a suitable dispersing medium, emulsions in which a solution with an effective amount of a substance dissolved therein is dispersed and emulsified in a suitable dispersing medium, powders, granules etc.

As preparations suitable for parenteral administration (e.g. intravenous injection, subcutaneous injection, intramuscular injection, local injection etc.), there are aqueous and non-aqueous isotonic sterile injection liquid preparations, and these may contain antioxidants, buffers, bacteriostatic agents, tonicity agent etc. In addition, the examples include aqueous and non-aqueous sterile suspensions, and these may contain solubilizers, thickeners, stabilizers, antiseptics etc. The preparation can be sealed into a container by a unit dose or a plurality of doses, like ampoules or vials. Alternatively, an active ingredient and a pharmaceutical acceptable carrier are lyophilized, and may be stored in the state where it may be dissolved or suspended in a suitable sterile vehicle immediately before use.

An administration method and a dosage form of the substance capable of inhibiting or eliminating the Th2 cell-like function of the IL-17RB positive NKT cell, which is an active component of the therapeutic agent of the present invention, are not particularly limited, but are intravenous administration, intra-arterial administration, intramuscular administration, oral administration, suppository administration etc., and the substance can be formulated into oral or parenteral administration by combining with pharmaceutically acceptable excipients or diluents. Administration is performed once or by dividing into several times per day, and an amount of dose is determined depending on the conditions such as severity, age, sex, weight etc. of a patient, and is in such a range that the side effect is not generated.

EXAMPLES

The present invention will be explained in detail below by way of Examples, but these Examples do not limit a scope of the present invention at all. In addition, reagents, devices and materials used in the present invention are commercially available, unless otherwise is indicated.

Example 1

Identification of IL-17RB

A gene predominantly expressed in an NKT cell was extracted, using the results of a DNA microarray of various immunocytes reported by RIKEN RCAI (Bioinformatics, in press, 2007) as reference database. As a result, it was revealed that IL-17RB (NM_019583, 1420789_at) has a higher gene expression level than other immunocytes in the NKT cell. A presumed open reading frame structure of IL-17RB is shown in SEQ ID No.: 1, and a presumed amino acid sequence is shown in SEQ ID No.: 2.

A primary structure of a presumed amino acid sequence of the present membrane molecule was subjected to hydropathy plot analysis according to the method of Kyte and Doolittle (J. Exp. Med., vol. 157, pp. 105-132, 1982) (FIG. 1). As a result, it was revealed that IL-17RB is an I-type transmembrane protein having a signal sequence at an N end. IL-17RB consists of 499 amino acid residues and, from the results of hydropathy plot analysis, it is presumed that IL-17RB has a signal sequence of 17 amino acid residues, an extracellular region of 265 amino acid residues, a transmembrane region of 23 amino acid residues, and an intracellular region of 194 amino acid residues. Further, from the results of homology search and motif search, it was revealed that the extracellular region has four sites of asparagine-bound glycosylated parts, and 10 cysteine residues, but a predicted steric structure was unknown. Further, it was revealed that IL-17RB has an SEFIR domain (329-476) in the intracellular region, it was predicted that IL-17RB is associated with an adapter molecule via this domain, and it was predicted that IL-17RB transmits a signal via this associated adapter molecule.

Example 2

Preparation of a Soluble Recombinant of IL-17RB (Soluble IL-17RB-Ig)

Figure 2:
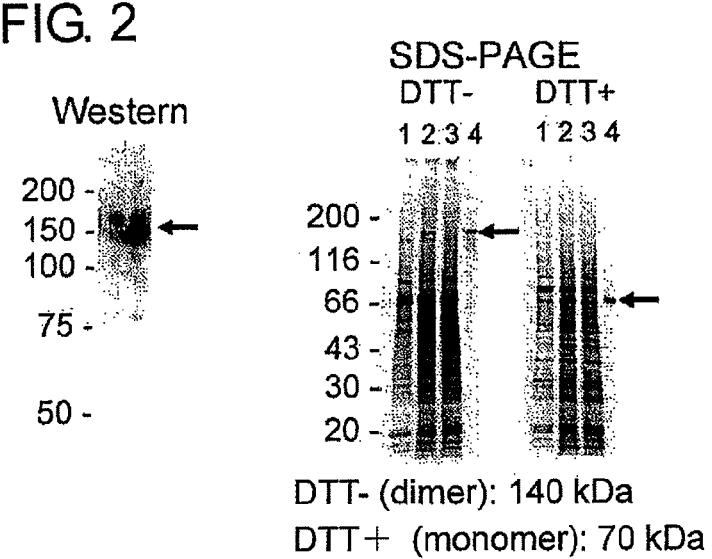
FIG. 2 is a view showing expression and purification of recombinant soluble IL-17RB-Ig.

From the result of hydropathy plot analysis (FIG. 1), a recombinant in which a region thought to be an extracellular domain and an Fc region of human IgG1 are bound was prepared. Note that, in order to prevent binding to an Fcγ receptor present on a surface of various cells, three positions of an Fc region of human IgG1 were subjected to amino acid replacement. Specifically, as the extracellular region, up to an amino acid position 282 of SEQ ID No.: 1 of IL-17RB was selected. A DNA sequence encoding this soluble recombinant is shown in SEQ ID No.: 3, and an amino acid sequence is shown in SEQ ID No.: 4. A site at which the amino acid replacement was performed in the Fc region corresponds to a position 302 (Leu→Ala), a position 303 (Leu→Glu) and a position 469 (Val→Asp). This gene was introduced into the pIRES2-EGFP vector (manufactured by Clontech), and this was transiently expressed in a 293T cell under control of a CMV promoter, and an expression product (IL-17RB soluble recombinant) was purified from the resulting culturing supernatant by affinity chromatography using a resin bound to Protein A having binding property to the Fc region (FIG. 2).

Example 3

Establishment of Specific Monoclonal Antibody to IL-17RB

Figure 3:
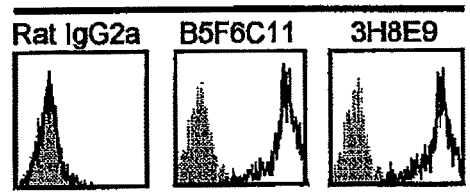
FIG. 3 is a view showing reactivity of an IL-17RB-specific monoclonal antibody (B5F6C11, 3H8E9) to an IL-17RB forcibly expressing cell strain.

The IL-17RB soluble recombinant described in Example 2 was immunized into a rat, and cell-fused with a rat myeloma cell strain P3U1 to obtain a specific monoclonal antibody-producing hybridoma. In screening, the recombinant described in Example 2 was solid-phased, a clone having reactivity was selected by an ELISA method and, at the same time, a specific monoclonal antibody was selected by analyzing reactivity to a 293T cell in which a full length of IL-17RB had been forcibly expressed, with a flow cytometer. The results of confirming reactivity between the culturing supernatant of the resulting monoclonal antibody-producing hybridoma (B5F6C11, 3H8E9) and the IL-17RB full length forcibly expressing strain are shown in FIG. 3.

Example 4

Searching of Reactivity of a Monoclonal Antibody on a Mouse Spleen Cell

Figure 4:
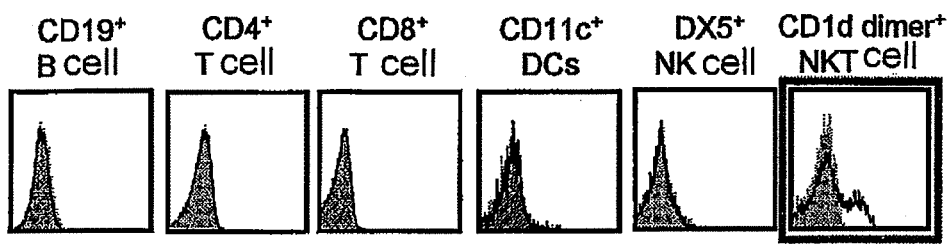
FIG. 4 is a view showing that IL-17RB is specifically expressed in an NKT cell.
Figure 5:
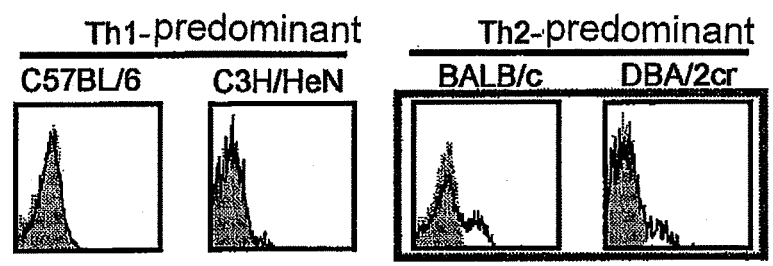
FIG. 5 is a view showing that IL-17RB is expressed in an NKT cell of a Th2 dominant mouse. It is not expressed in an NKT cell of a Th1 dominant mouse.
Figure 6:
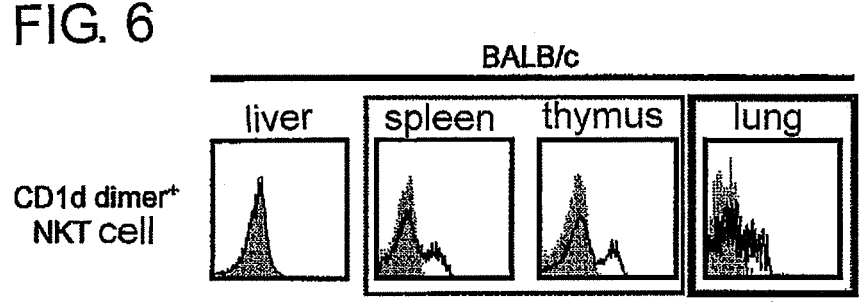
FIG. 6 is a view showing the results of investigation of a presentation pattern in each organ of an IL-17RB positive NKT cell. The IL-17RB positive NKT cell is present in lung at a large amount.

Using the monoclonal antibody established by the technique described in Example 3, localization of expression of IL-17RB was confirmed. The monoclonal antibody was biotinated, and acted on a Balb/c mouse spleen-derived leukocyte, and phycoerythrin-bound avidin was reacted, whereby a cell expressing IL-17RB was confirmed. In an unstimulated cell, it was confirmed that a part of an α-GalCer/CD1d dimer positive invariant NKT cell has reactivity (FIG. 4). On the other hand, expression of IL-17RB could not be confirmed in immunocytes such as a B cell, a T cell, a dendritic cell, an NK cell etc. (FIG. 4). Further, when expression of IL-17RB in an invariant NKT cell in various lineage mice was confirmed, expression was seen in Balb/c and DBA/2cr known to be a Th2 predominant mouse, but little expression was seen in C57BL/6 and C3H/HeN known to be a Th1 predominant mouse (FIG. 5). Then, an existence manner in various organs of the IL-17RB positive NKT cell in a Balb/c mouse was confirmed. A cell suspension was prepared from each organ, and an IL-17RB positive NKT cell among the α-GalCer/CD1d dimer positive NKT cell was detected using the monoclonal antibody obtained in Example 3. As a result, it was revealed that a number of cells are present in a lung among the confirmed organs, and the cell is present in spleen and thymus, but is not present in liver (FIG. 6).

Example 5

Analysis of a Surface Antigen of the IL-17RB Positive NKT Cell

Figure 7:
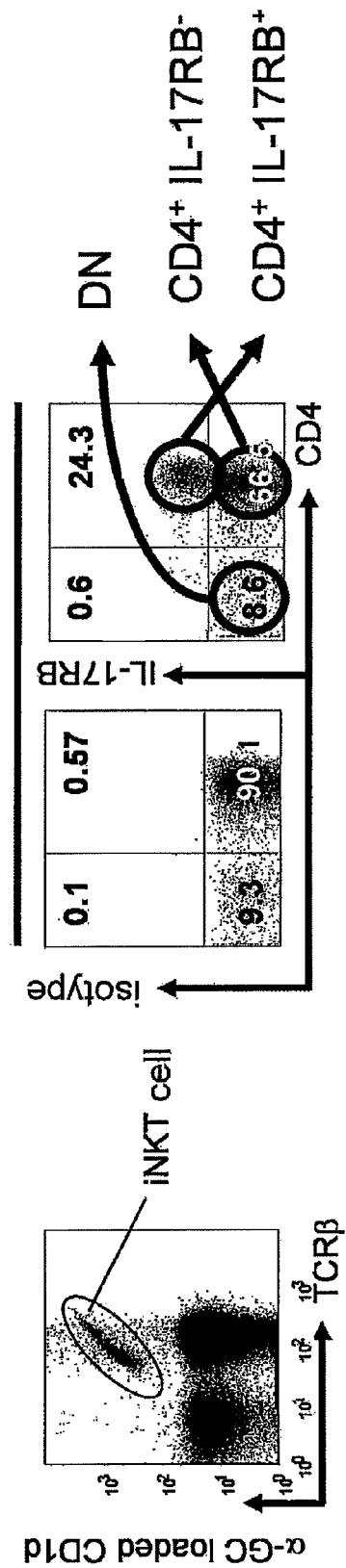
FIG. 7 is a view showing that IL-17RB is expressed in a CD4 positive NKT cell.
Figure 8:
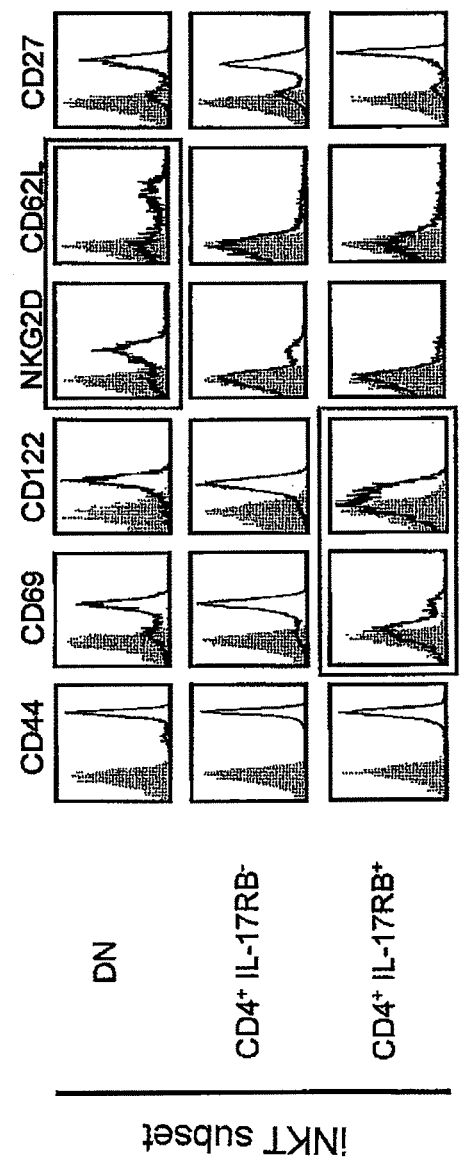
FIG. 8 is a view showing the results of investigation of an expression profile of a surface marker of an NKT cell subset.

Based on a report that the NKT cell is classified into functionally different two subsets (CD4 positive and DN) using CD4 as a marker (J. Exp. Med., vol. 202, pp. 1279-1288, 2005), an expression manner of a surface antigen in the NKT cell of IL-17RB was investigated by FACS analysis using the monoclonal antibody described in Example 3, and an antibody of each surface antigen. As a result, it was revealed that IL-17RB is expressed mainly in a CD4 positive NKT cell, and about ⅓ of the CD4 positive NKT cell is IL-17RB positive (FIG. 7). That is, it was shown that the NKT cell is classified into three subsets of (A) CD4 negative IL-17RB negative (DN), (B) CD4 positive IL-17RB negative, and (C) CD4 positive IL-17RB positive. Then, regarding three subsets of (A), (B) and (C), an expressed surface antigen was analyzed (FIG. 8). As a result, the finding that expression of CD69 and CD122 is low in (C) as compared with (A) and (B), and (C) is killer receptor NKG2D negative, and CD62L negative etc. was obtained.

For CD4 expression, a Pacific Blue-labeled anti-mouse CD4 antibody (RM4-5, manufactured by BD Biosciences) was used. For CD69 expression, a phycoerythrin-labeled anti-mouse CD69 antibody (H1. 2F3, manufactured by BD Biosciences) was used. For CD122 expression, a phycoerythrin-labeled anti-mouse CD122 antibody (TM-β1, manufactured by BD Biosciences) was used. For NKG2D expression, a phycoerythrin-labeled anti-mouse NKG2D antibody (C7, manufactured by eBioscience) was used. For CD62L expression, a phycoerythrin-labeled anti-mouse CD62L antibody (BVD6-24G2, manufactured by eBioscience) was used.

Example 6

Analysis of Gene expression of the IL-17RB Positive NKT Cell

Figure 9:
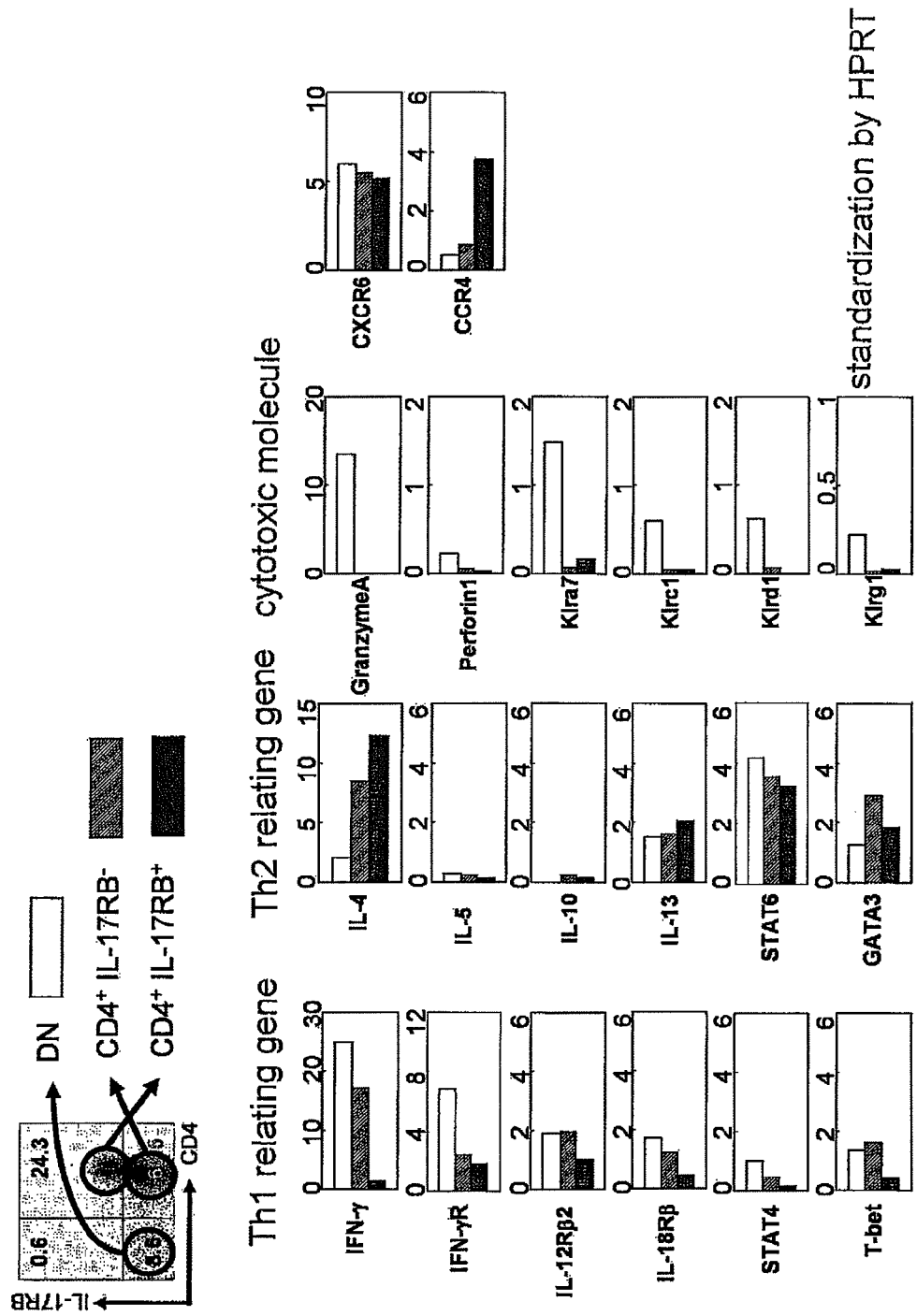
FIG. 9 is a view showing the results of investigation of an expression profile of an NKT cell subset gene.

Regarding three subsets of the NKT cell identified in Example 5, an mRNA was prepared, and a relative gene expression level was confirmed by a quantitative PCR method (FIG. 9). Preparation of the mRNA and quantitative PCR were performed using the method usually carried out in the art. Specifically, Platinum SYBR Green quantitative PCR (manufactured by Invitrogen) was used and, as a primer, a combination described in Table 1 was used. As a result, it was revealed that in (C), expression of a gene group defining the Th1 cell is relatively low as compared with (A) and (B), and expression of a gene group defining the Th2 cell is equivalent or relatively high as compared with (A) and (B). In addition, it was revealed that expression of a gene group associated with the cytotoxic activity is seen only in (A). Further, it was revealed that expression of a chemokine receptor CCR4 is high in (C) as compared with (A) and (B). When the results of Example 5 and Example 6 are taken into consideration together, it was revealed that the IL-17RB positive NKT cell is very similar in phenotype to the Th2 cell.

Genes defining the Th1 cell and genes defining the Th2 cell, genes associated with the cytotoxic activity, and chemokine.chemokine receptor genes, which were detected, together with primer information for detecting them are summarized in Table 1. In addition, expression of each gene was standardized by expression of the HPRT gene.

TABLE 1

| | | Sense | Antisense |
|---|---|---|---|
| Genes defining Th1 cell | IFN-γ | SEQ ID No.: 5 | SEQ ID No.: 6 |
| | IFN-γR | SEQ ID No.: 7 | SEQ ID No.: 8 |
| | IL-12Rβ2 | SEQ ID No.: 9 | SEQ ID No.: 10 |
| | IL-18Rβ | SEQ ID No.: 11 | SEQ ID No.: 12 |
| | STAT4 | SEQ ID No.: 13 | SEQ ID No.: 14 |
| | T-bet | SEQ ID No.: 15 | SEQ ID No.: 16 |
| Genes defining Th2 cell | IL-4 | SEQ ID No.: 17 | SEQ ID No.: 18 |
| | IL-5 | SEQ ID No.: 19 | SEQ ID No.: 20 |
| | IL-10 | SEQ ID No.: 21 | SEQ ID No.: 22 |
| | IL-13 | SEQ ID No.: 23 | SEQ ID No.: 24 |
| | STAT6 | SEQ ID No.: 25 | SEQ ID No.: 26 |
| | GATA3 | SEQ ID No.: 27 | SEQ ID No.: 28 |
| Genes associated with cytotoxic activity | GranzymeA | SEQ ID No.: 29 | SEQ ID No.: 30 |
| | Perforin1 | SEQ ID No.: 31 | SEQ ID No.: 32 |
| | Klra7 | SEQ ID No.: 33 | SEQ ID No.: 34 |
| | Klrc1 | SEQ ID No.: 35 | SEQ ID No.: 36 |
| | Klrd1 | SEQ ID No.: 37 | SEQ ID No.: 38 |
| | Klrg1 | SEQ ID No.: 39 | SEQ ID No.: 40 |
| Chemokine• Chemokine receptor genes | CXCR6 | SEQ ID No.: 41 | SEQ ID No.: 42 |
| | CCR4 | SEQ ID No.: 43 | SEQ ID No.: 44 |
| | TARC/CCL17 | SEQ ID No.: 45 | SEQ ID No.: 46 |
| | MDC/CCL22 | SEQ ID No.: 47 | SEQ ID No.: 48 |
| Genes defining Th17 cell | IL-17A | SEQ ID No.: 49 | SEQ ID No.: 50 |
| | RORγt | SEQ ID No.: 51 | SEQ ID No.: 52 |

Example 7

In vitro Assessment of Function of the IL-17RB Positive NKT Cell (1)

Figure 10:
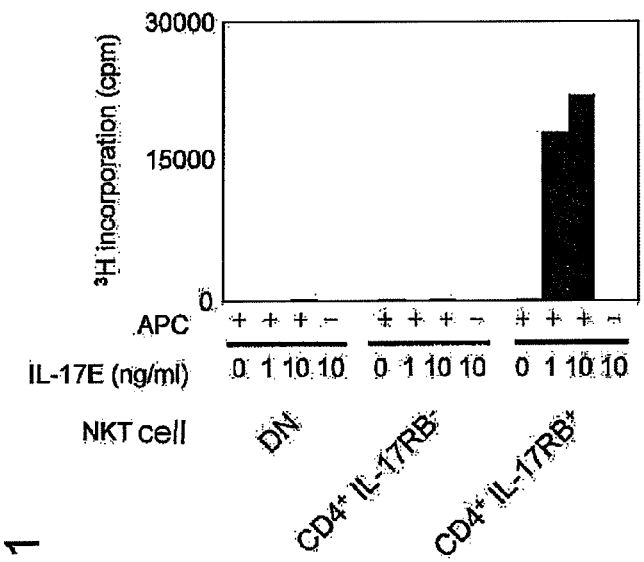
FIG. 10 is a view showing that an IL-17RB positive NKT cell is proliferated ligand-dependently.
Figure 11:
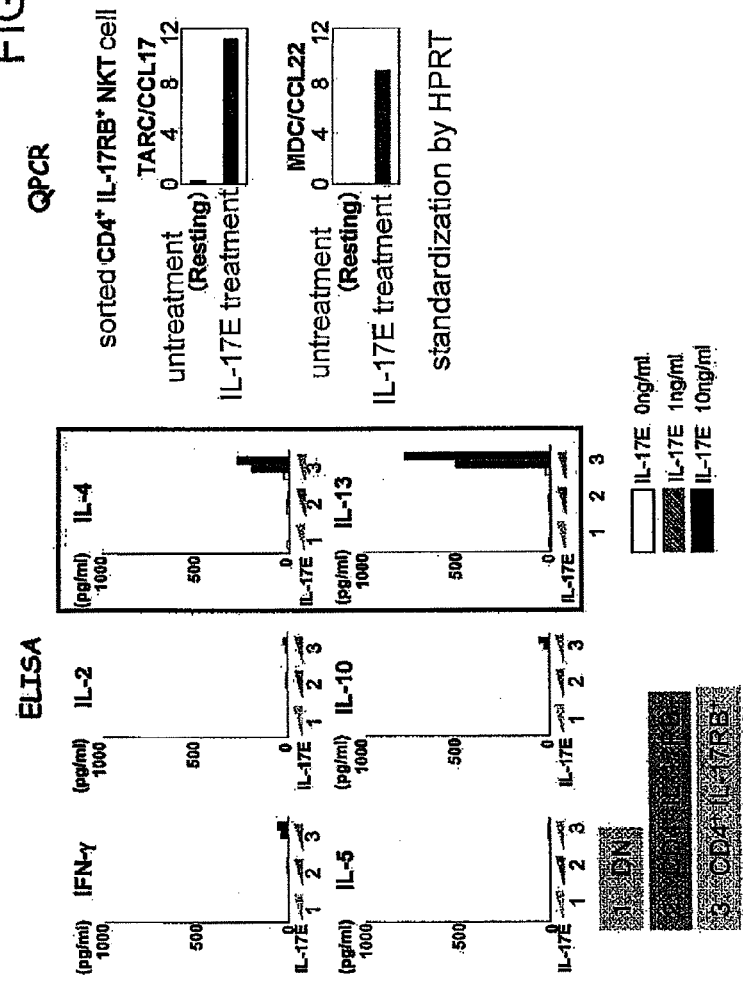
FIG. 11 is a view showing that an IL-17RB positive NKT cell produces a large amount of a Th2 cytokine/chemokine ligand-dependently.

As a ligand to IL-17RB, IL-17E/IL-25 is known (J. Biol. Chem., vol. 276, pp. 1660-1664, 2001). Then, regarding the three subsets of (A), (B) and (C) described in Example 5, reactivity to IL-17E/IL-25 was confirmed. As a result, the IL-17E/IL-25-dependent cell proliferation activity was seen only in (C) (FIG. 10). Cell proliferation was measured by uptake of $^3$H. Further, it was revealed that an IL-17E/IL-25-dependent reaction leads to production of a large amount of Th2 cytokine/chemokine such as IL-13, IL-4, TARC/CCL17, MDC/CCL22, from (C) (FIG. 11). Regarding IFN-γ, IL-5, IL-2, IL-10, IL-4 and IL-13, measurement was performed by an ELISA method using an antibody of each cytokine/chemokine and, regarding TARC/CCL17 and MDC/CCL22, measurement was performed by a quantitative PCR method using a primer to each chemokine gene. A combination of respective primers is shown in the Table 1. In addition, in the quantitative PCR method, expression was standardized by expression of an HPRT gene. This result shows that the IL-17RB positive NKT cell is proliferated IL-17E/IL-25-dependently, and has the ability to produce Th2 cytokine/chemokine.

Examples 8

In vivo Assessment of Function of the IL-17RB Positive NKT Cell

Figure 12:
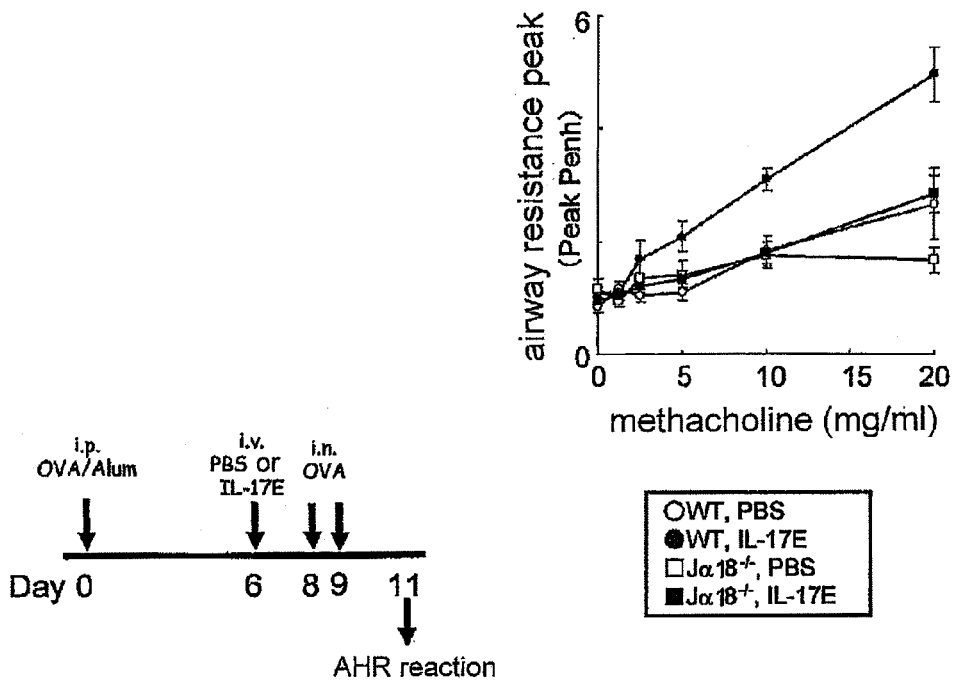
FIG. 12 is a view showing that an airway resistance value is increased NKT cell-dependently by administration of a ligand.
Figure 13:
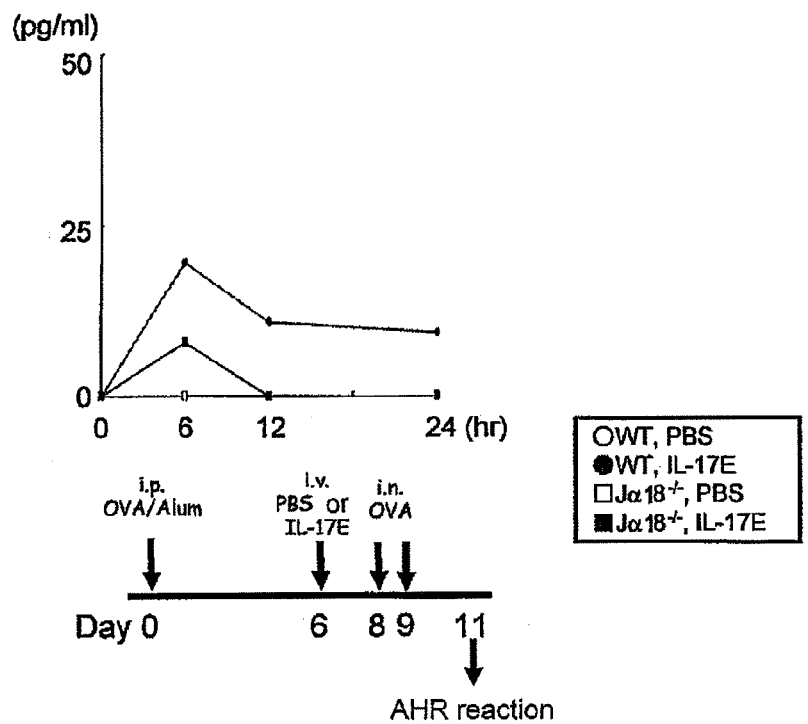
FIG. 13 is a view showing that IL-13 is produced NKT cell-dependently by administration of a ligand.

As described in Example 7, since the IL-17RB positive NKT cell produces a cytokine which becomes important in pathogenesis of allergic airway inflammation and airway hypersensitivity, particularly, IL-13, a role of the cell in an asthma model was revealed. A Balb/c mouse or an NKT cell-deficient mouse established by the present inventors (Jα18-deficient mouse) (Balb/c background) (Science, vol. 278, pp. 1623-1626, 1997) was subcutaneously immunized with OVA/Alum, and intravenously injected with IL-17E/IL-25 or PBS (control), OVA was pernasally administered again, and a methacholine stimulation-induced airway resistance was measured. As a result, IL-17E/IL-25-dependent increase in an airway resistance value was seen in the Balb/C mouse, while increase in an airway resistance value by administration of IL-17E/IL-25 was not seen in the NKT cell-deficient mouse (FIG. 12). Further, increase in an IL-13 concentration in blood was seen in the IL-17E/IL-25-treated Balb/c mouse, but little increase was seen in the NKT cell-deficient mouse, correlating with an airway resistance value (FIG. 13).

Example 9

Analysis of IL-17RB-Expressing Cell

Figure 14:
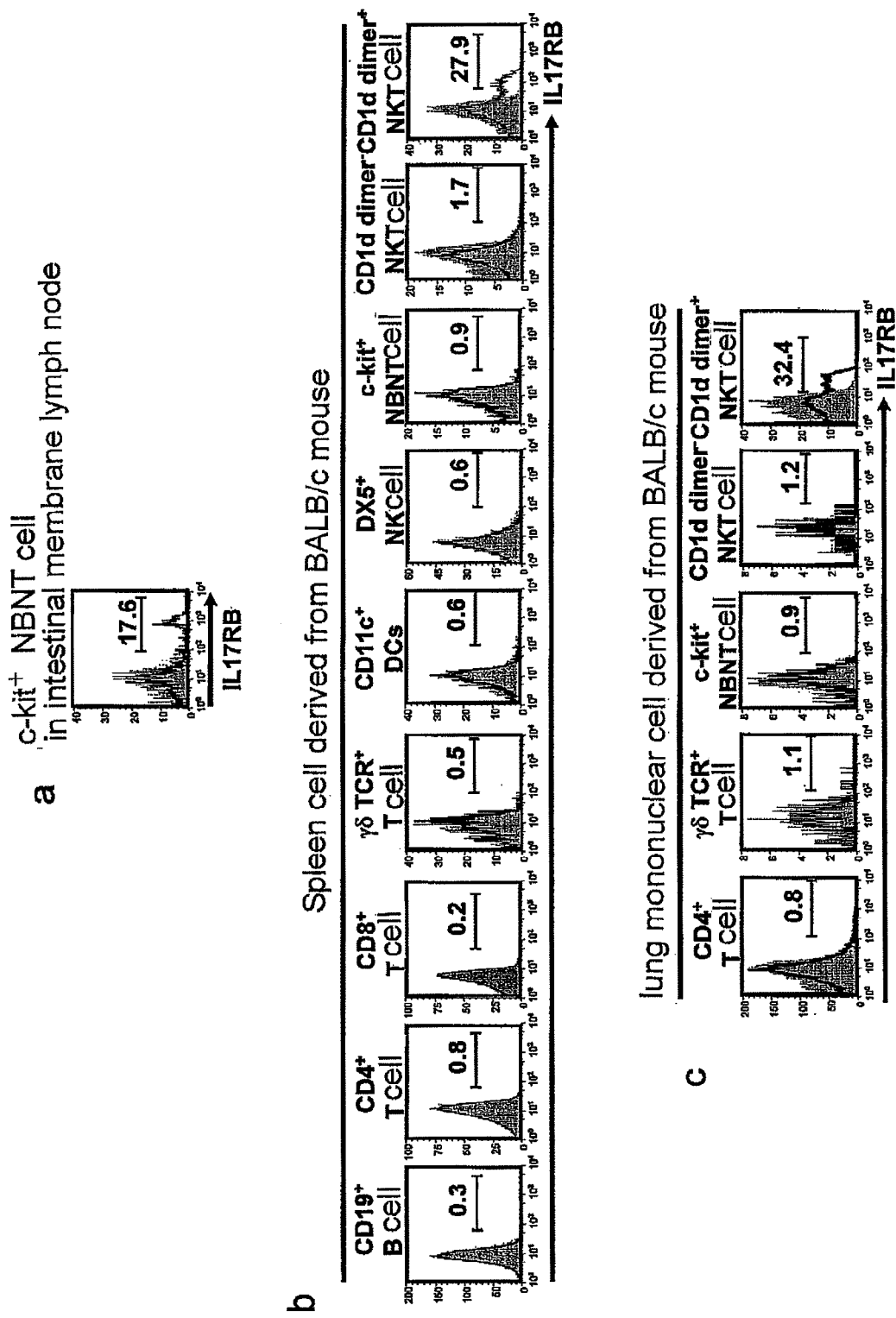
FIG. 14 is a view showing the results of analysis regarding an expression manner of IL-17RB in various cells.

Using the mouse IL-17RB specific monoclonal antibody established by the technique described in Example 3, an expression manner of IL-17RB in a spleen cell and a mononuclear cell of lung was analyzed in detail. Since there has previously been a report that expression of IL-17RB is seen in a c-kit positive non-B non-T cell (c-kit+NBNT cell) of an intestinal membrane lymph node (MLN) (Fallon, P. G., S. J. Ballantyne, N. E. Mangan, J. L. Barlow, A. Dasvarma, D. R. Hewett, A. McIlgorm, H. E. Jolin, and A. N. McKenzie 2006. Identification of an interleukin (IL)-25-dependent cell population that provides IL-4, IL-5, and IL-13 at the onset of helminth expulsion. J. Exp. Med. 203: 1105-1116), when staining property of the present cell was confirmed using the antibody of the present invention, it was confirmed that about 20% of cells are positive (FIG. 14a). Then, using the present antibody, expression of each subset of a spleen cell and a mononuclear cell of lung was confirmed. The expression was investigated by FACS analysis using the monoclonal antibody described in Example 3, and an antibody of each surface antigen peculiar to each subset. As a result, in any of the spleen cell (FIG. 14b) and the lung mononuclear cell (FIG. 14c), expression was confirmed only in a part of a CD1d restricted NKT cell, and localization of expression of IL-17RB was revealed.

Example 10

Analysis of Gene Expression of the IL-17RB Positive NKT Cell

Figure 15:
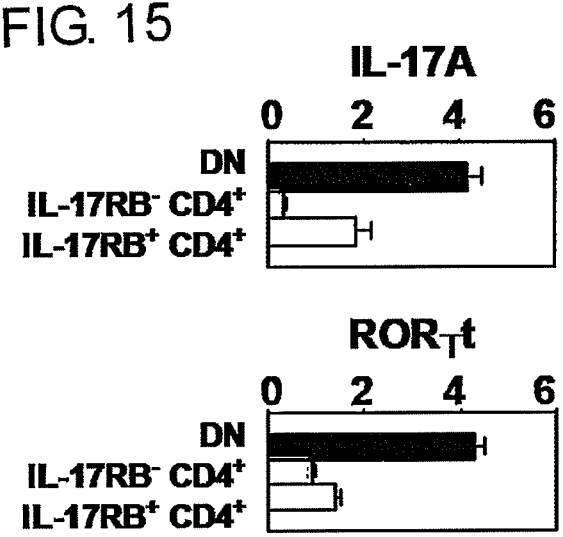
FIG. 15 is a view showing the results of investigation of an expression profile of an NKT cell subset gene (IL-17/IL-17A, RORγt).

In Example 5, it was shown that the NKT cell is classified into three subsets of (A) CD4 negative IL-17RB negative (DN), (B) CD4 positive IL-17RB negative, and (C) CD4 positive IL-17RB positive. Regarding these three subsets of the NKT cell, an mRNA was prepared, and a relative gene expression level by a quantitative PCR method was further confirmed. An IL-17-producing helper T cell (Th17) recognized as a new subset of a T cell has a transcription factor RORγt as a master gene. Then, when the mRNA of IL-17(IL-17A) and RORγt was confirmed by quantitative PCR, it was revealed that the mRNA is significantly higher in (A) than in (B) and (C). This result shows that (C) is a cell group which is different from the already reported IL-17-producing NKT cell (Michel, M. L., A. C. Keller, C. Paget, M. Fujio, F. Trottein, P. B. Savage, C. H. Wong, E. Schneider, M. Dy, and M. C. Leite-de-Moraes. 2007. Identification of an IL-17-producing NK1.1(neg) iNKT cell population involved in airway neutrophilia. J. Exp. Med. 204: 995-1001), and strongly suggests that the IL-17RB positive NKT cell is a newly identified cell population (FIG. 15).

In the present Example, the quantitative PCR was performed by the same procedure as that of Example 6. Primer information of genes defining the Th17 cell to be detected is shown in Table 1.

Example 11

In vitro Assessment of the Function of the IL-17RB Positive NKT Cell (2)

Figure 16:
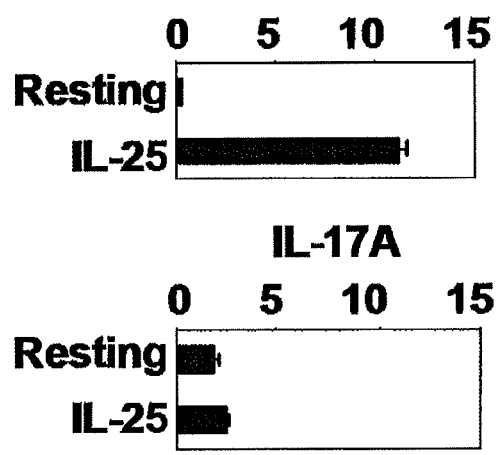
FIG. 16 is a view showing that an IL-17RB positive NKT cell produces a large amount of eosinophil chemotactic factor-L (ECF-L) ligand-dependently.

Regarding the three subsets of (A), (B), and (C) described in Example 10, reactivity with IL-17E/IL-25 was confirmed. As a result, it was shown that (C) the IL-17RB positive NKT cell produces a large amount of eosinophil chemotactic factor-L (ECF-L) IL-17E/IL-25-dependently (FIG. 16, upper column). This result shows that the function of locally mobilizing IL-5-producing eosinophil is possessed, and it was suggested that an activated IL-17RB positive NKT cell induces indirect eosinophilia IL-17E/IL-25-dependently. In addition, it was also revealed that expression of IL-17A changed little before and after IL-25 stimulation (FIG. 16, lower column).

Example 12

Figure 17:
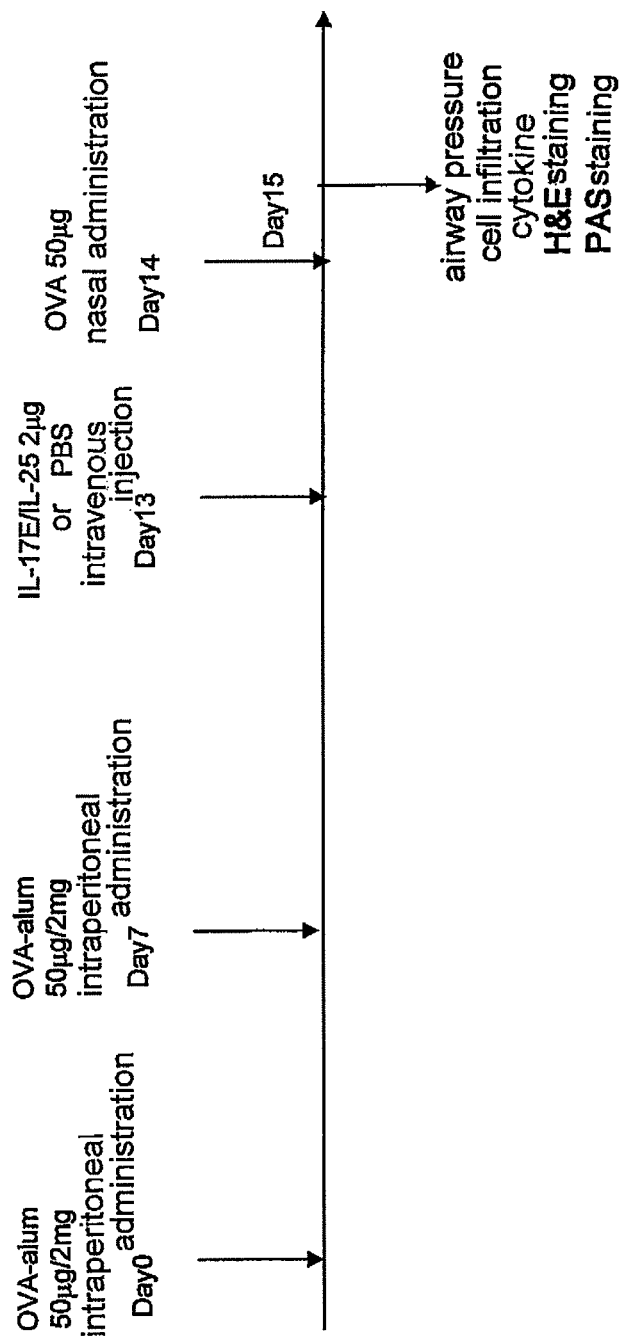
FIG. 17 is a view showing a protocol of an experiment which was performed for elucidating a role of an IL-17RB positive NKT cell in ligand-dependent airway hypersensitivity pathogenesis.

Elucidation of Role of the IL-17RB Positive NKT Cell in IL-17E/IL-25-Dependent Airway Hypersensitivity Pathogenesis As an asthma model in a mouse, there is an airway inflammation model using ovalbumin (OVA). In this model, after immunization with OVA-alum, OVA is inhaled to cause airway inflammation. Usually, by immunizing with OVA-alum (100 μg/2 mg) intraperitoneally two to three times at an interval of one week, and administering OVA (100 μg) by rhinenchysis for 3 days, methacholine-inducing airway inflammation can be developed. In the present Example, in order to confirm the action of IL-17E/IL-25, the action of IL-17E/IL-25 in a Balb/c mouse (WT) and an NKT cell-deficient mouse (Jα18KO mouse, Jα18$^{-/-}$) was confirmed in the condition for no observation of development of mathacholine-inducing airway inflammation, under which a mouse is immunized with OVA-alum (50 μg/2 mg) intraperitoneally two times at an interval of one week, and OVA (50 μg) is administered by rhinenchysis once. A series of protocol is shown in FIG. 17.

Figure 18:
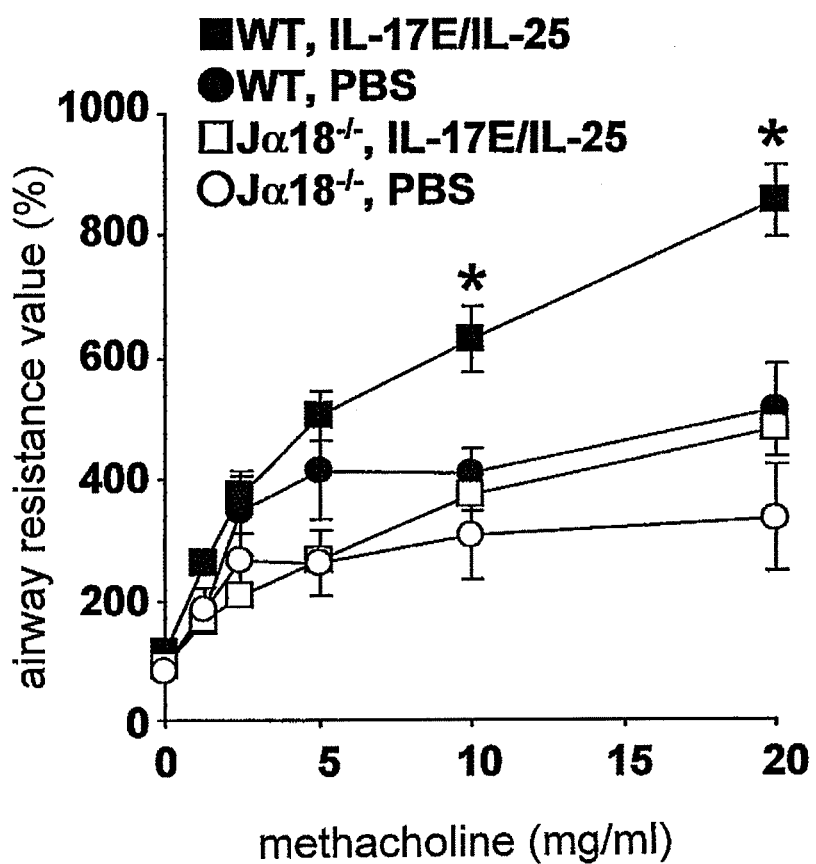
FIG. 18 is a view showing that increase in an airway resistance value by ligand administration is inhibited in an NKT-cell deficient mouse.
Figure 19:
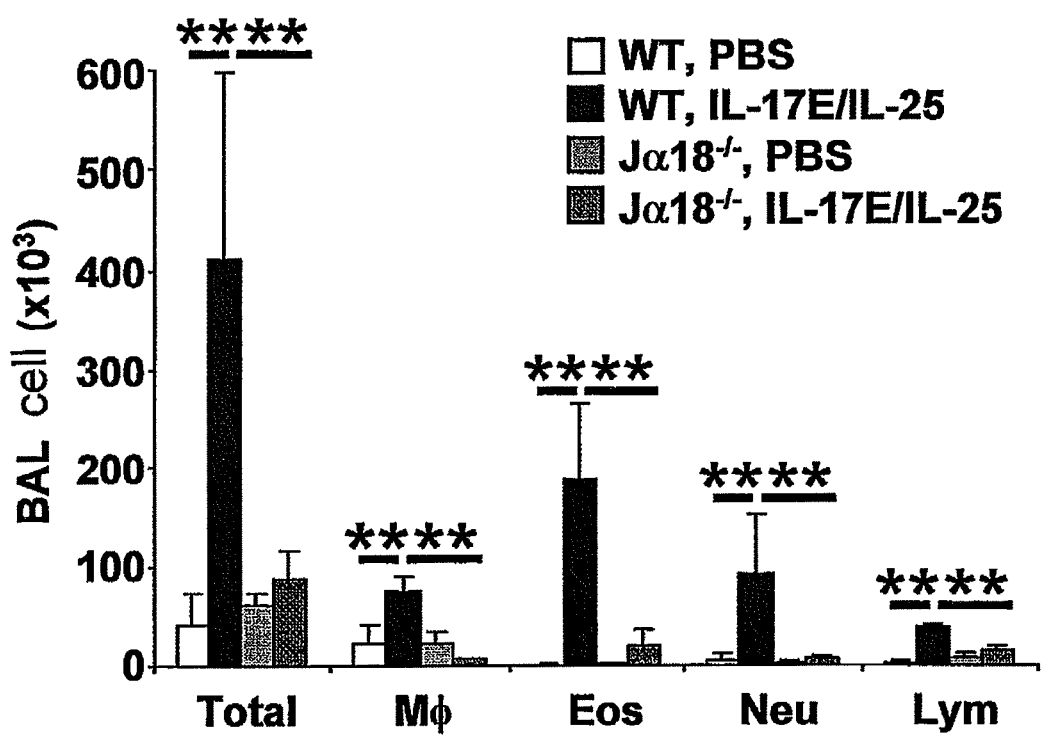
FIG. 19 is a view showing that cell infiltration into an alveolus fluid by ligand administration is inhibited in an NKT cell-deficient mouse.
Figure 20:
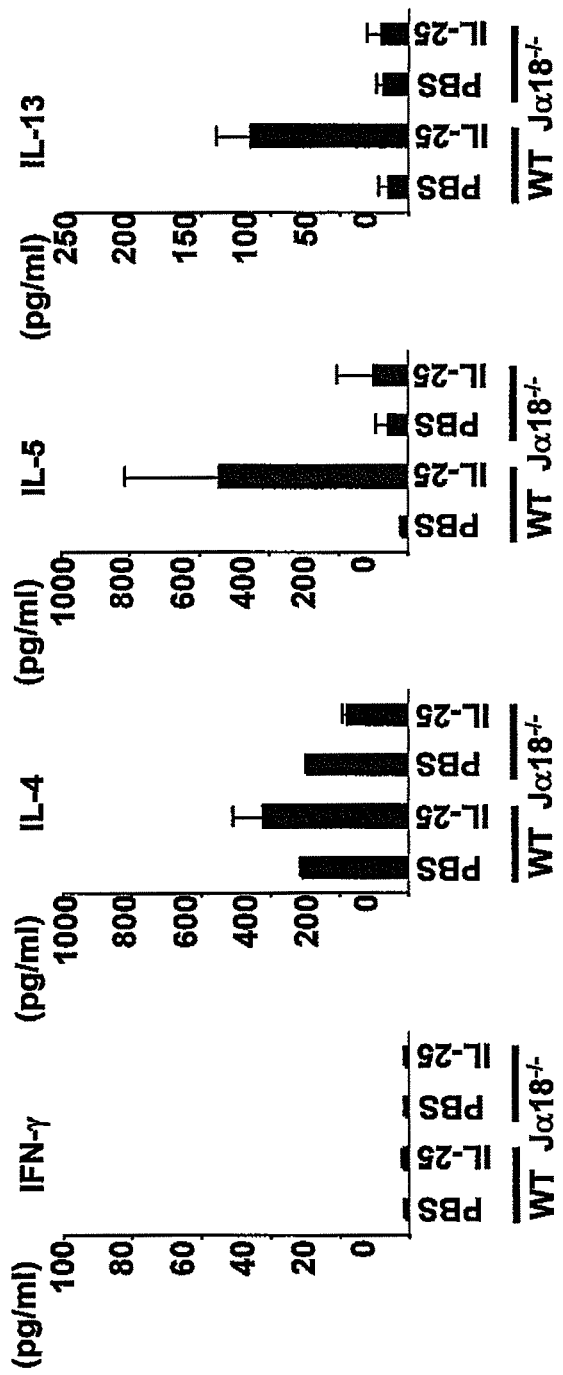
FIG. 20 is a view showing that production of IL-4 and IL-5 by ligand administration is inhibited in an NKT cell-deficient mouse.
Figure 21:
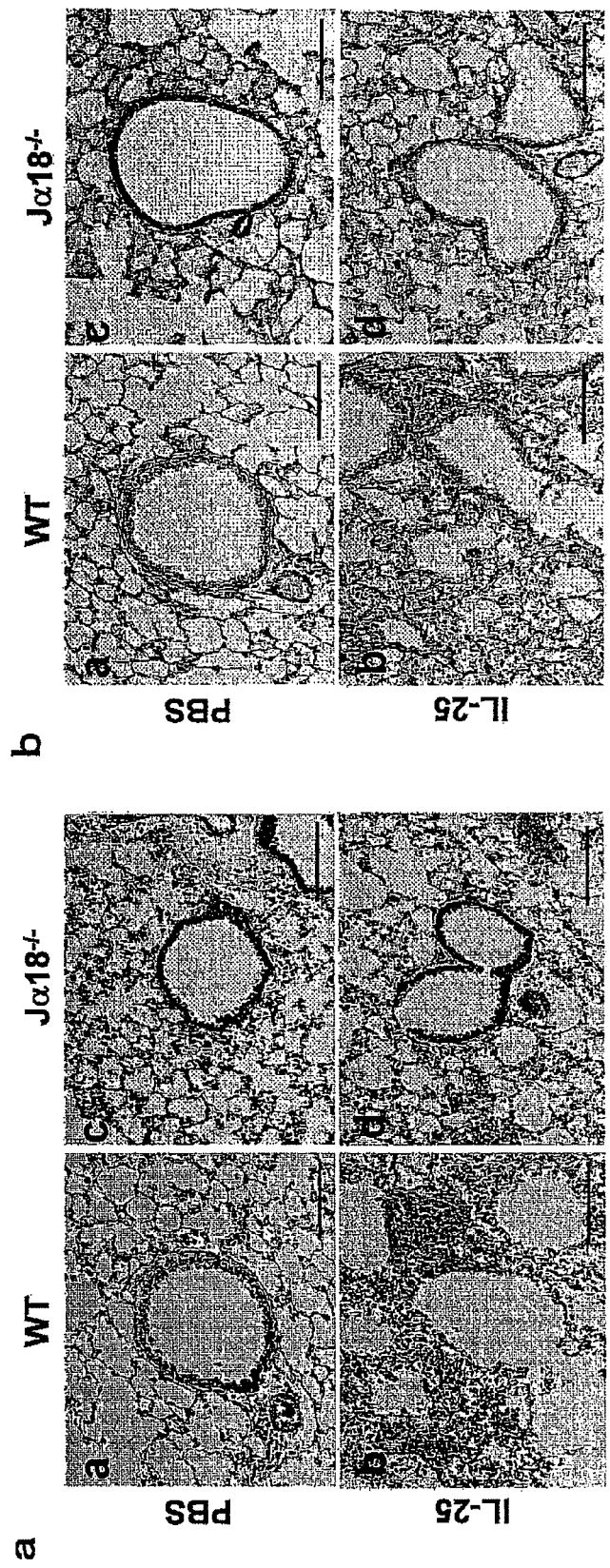
FIG. 21 is a view showing the results of investigation of infiltration (FIG. 21a) and mucin mucosal fluid overproduction (FIG. 21b) of eosinophil and neutrophil by ligand administration. A Balb/c mouse (WT) or an NKT-deficient mouse (Jα18$^{-/-}$) were investigated.
Figure 22:
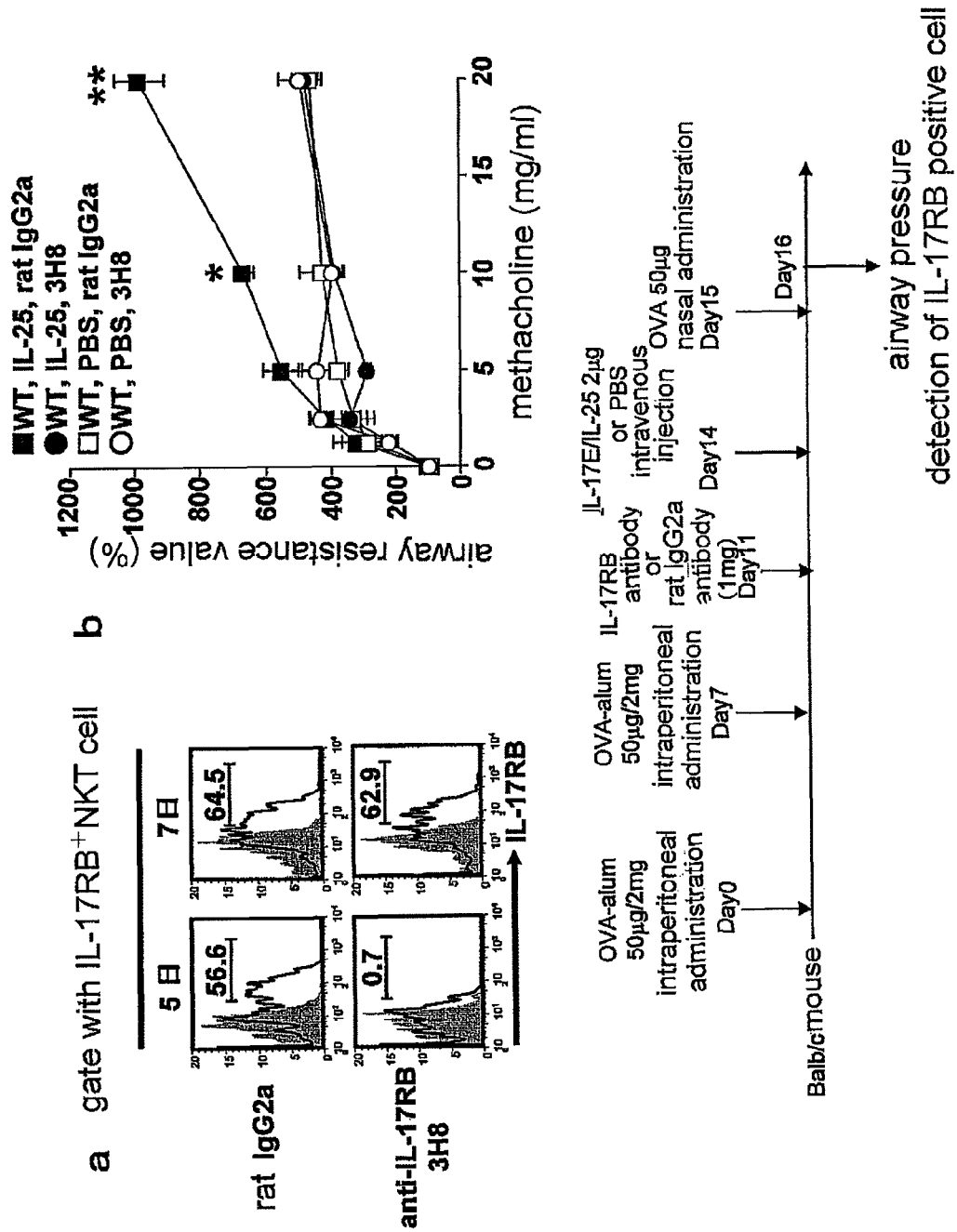
FIG. 22 is a view showing that increase in an airway resistance value by ligand administration can be inhibited by eliminating an IL-17RB positive NKT cell with an anti-IL-17RB antibody.
Figure 23:
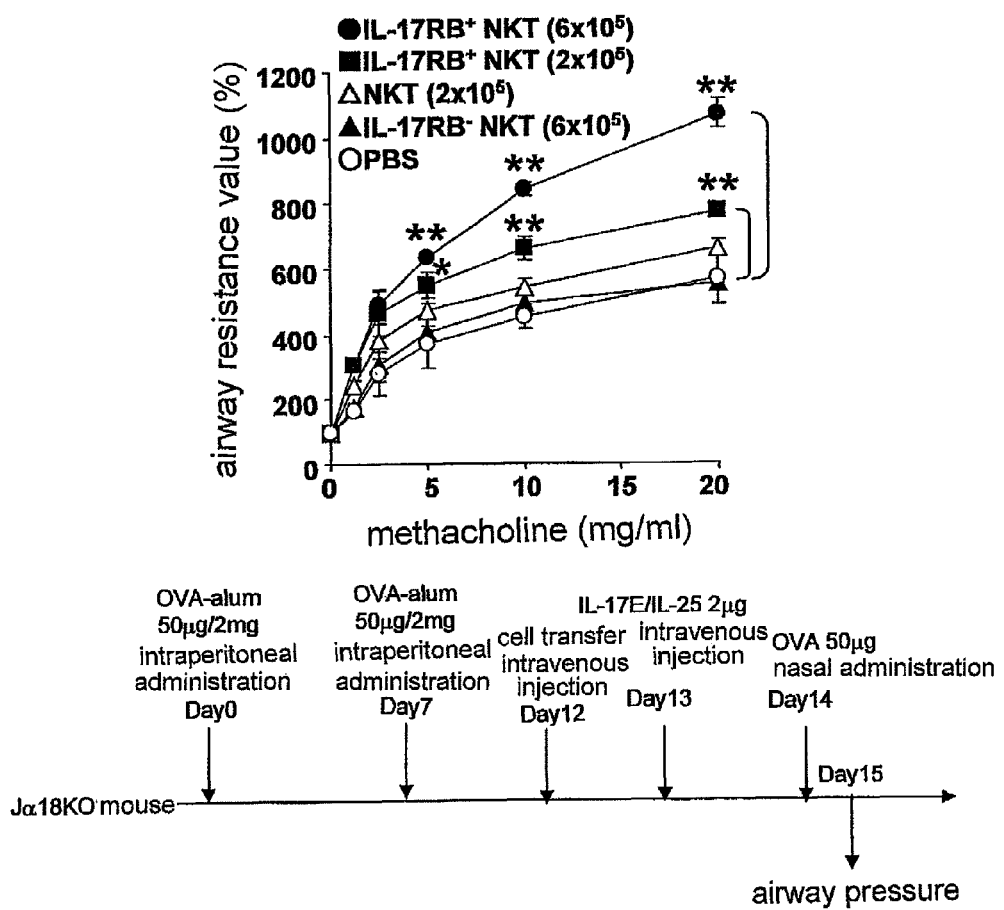
FIG. 23 is a view showing that increase in an airway resistance value by ligand administration was confirmed by transferring an IL-17RB positive NKT cell into an NKT cell-deficient mouse.

When development of airway inflammation was confirmed using increase in an airway pressure as an index in the present model, IL-17E/IL-25-dependent airway inflammation was developed in a Balb/c mouse, but was not developed in an NKT cell-deficient mouse (FIG. 18). Under the present condition, when cell infiltration into an alveolus washing solution after OVA inhalation was confirmed, remarkable infiltration was confirmed in a control mouse as compared with the NKT cell-deficient mouse, in an IL-17E/IL-25-administored group, in any of the total number (Total), macrophage (M$_T$), eosinophil (Eos), neutrophil (Neu), and a lymphocyte (Lym) (FIG. 19). Further, also regarding a cytokine concentration in an alveolus washing solution, the same tendency was strongly recognized with respect to IL-13 and IL-4 (FIG. 20). A tissue section was prepared from a lung tissue of these mice with a, microtome, and the section was investigated by hematoxylin.eosin staining, and PAS staining. As a result, infiltration of eosinophil.neutrophil (hematoxylin.eosin staining (FIG. 21a)) and mucin mucosal fluid overproduction (PAS staining (FIG. 22b)) were confirmed in an IL-17E/IL-25-administered control mouse. These results suggest that the IL-17RB positive NKT cell has a central role in IL-17E/IL-25-dependent airway hypersensitivity pathogenesis. In addition, in the above model, by eliminating the IL-17RB positive NKT cell with an anti-IL-17RB antibody before administration of IL-17E/IL-25, a role of the IL-17RB positive NKT cell was confirmed (FIG. 22). It was confirmed by FACS analysis that the IL-17RB positive NKT cell has been eliminated (FIG. 22a). By elimination of the IL-17RB positive NKT cell, it was seen that IL-17E/IL-25-dependent airway inflammation is inhibited also in a Balb/c mouse (FIG. 22b). Further, a role of an IL-17RB positive NKT cell was confirmed in a system in which the IL-17RB positive NKT cell was transferred into an NKT cell-deficient mouse before administration of IL-17E/IL-25. By transferring an IL-17RB positive NKT cell into an NKT cell-deficient mouse before administration of IL-17E/IL-25, observation of cell number-dependent exacerbation of airway inflammation was also confirmed (FIG. 23).

Example 13

Figure 24:
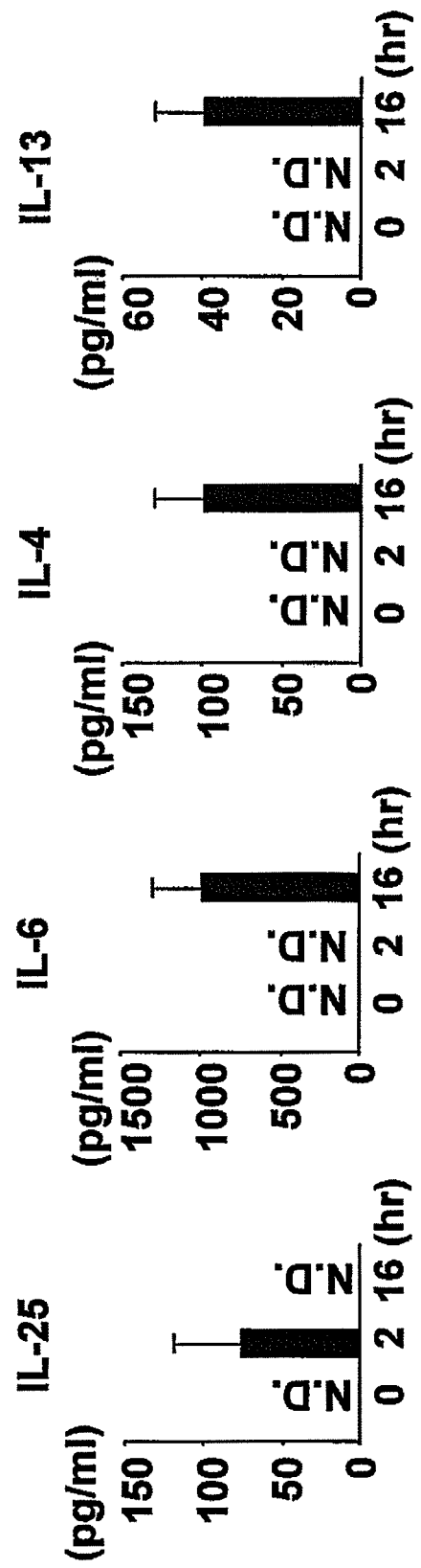
FIG. 24 is a view showing the measurement results of a concentration of IL-25, IL-6, IL-4 or IL-13 in an alveolus washing solution of an RSV-infected mouse.
Figure 25:
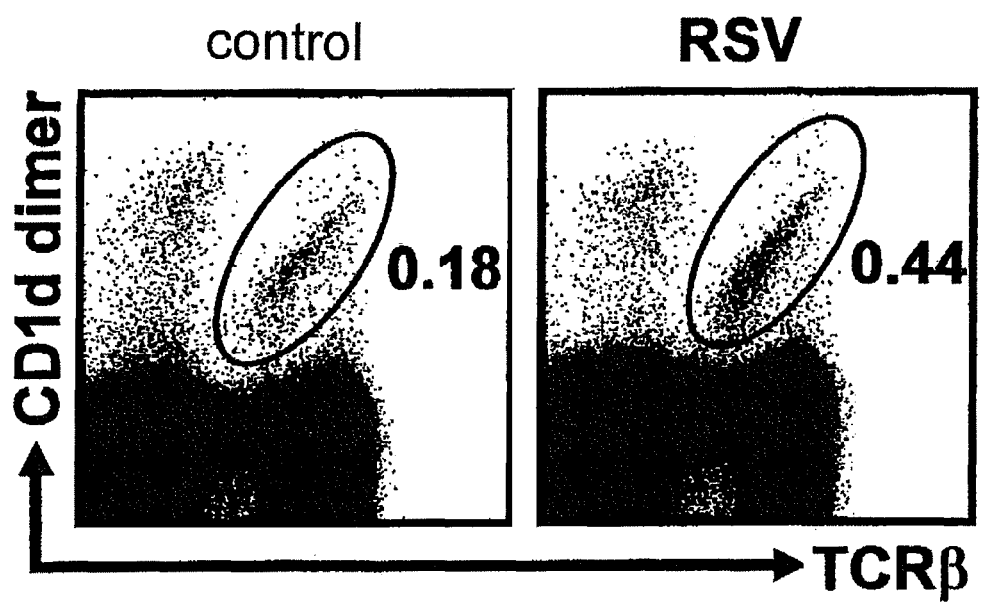
FIG. 25 is a view showing that an NKT cell is infiltrated into an alveolus fluid by RSV infection.
Figure 26:
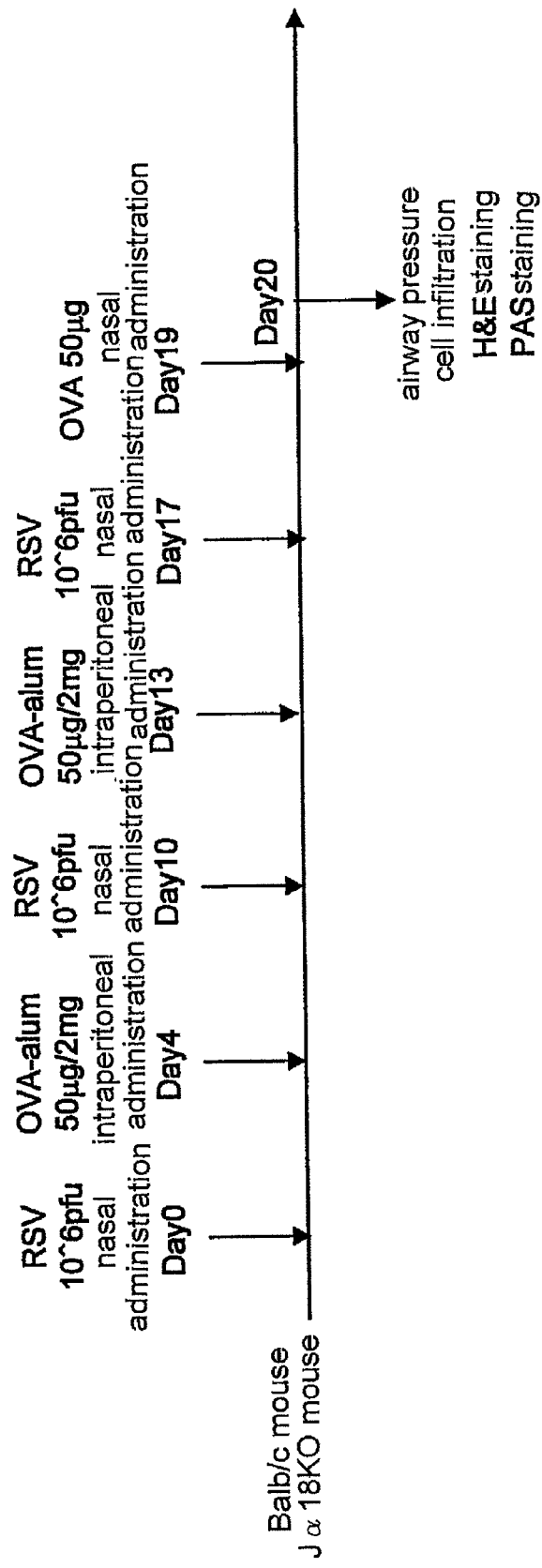
FIG. 26 is a view showing a protocol for analyzing involvement of an IL-17RB positive NKT cell in RSV-dependent airway hypersensitivity pathogenesis.
Figure 27:
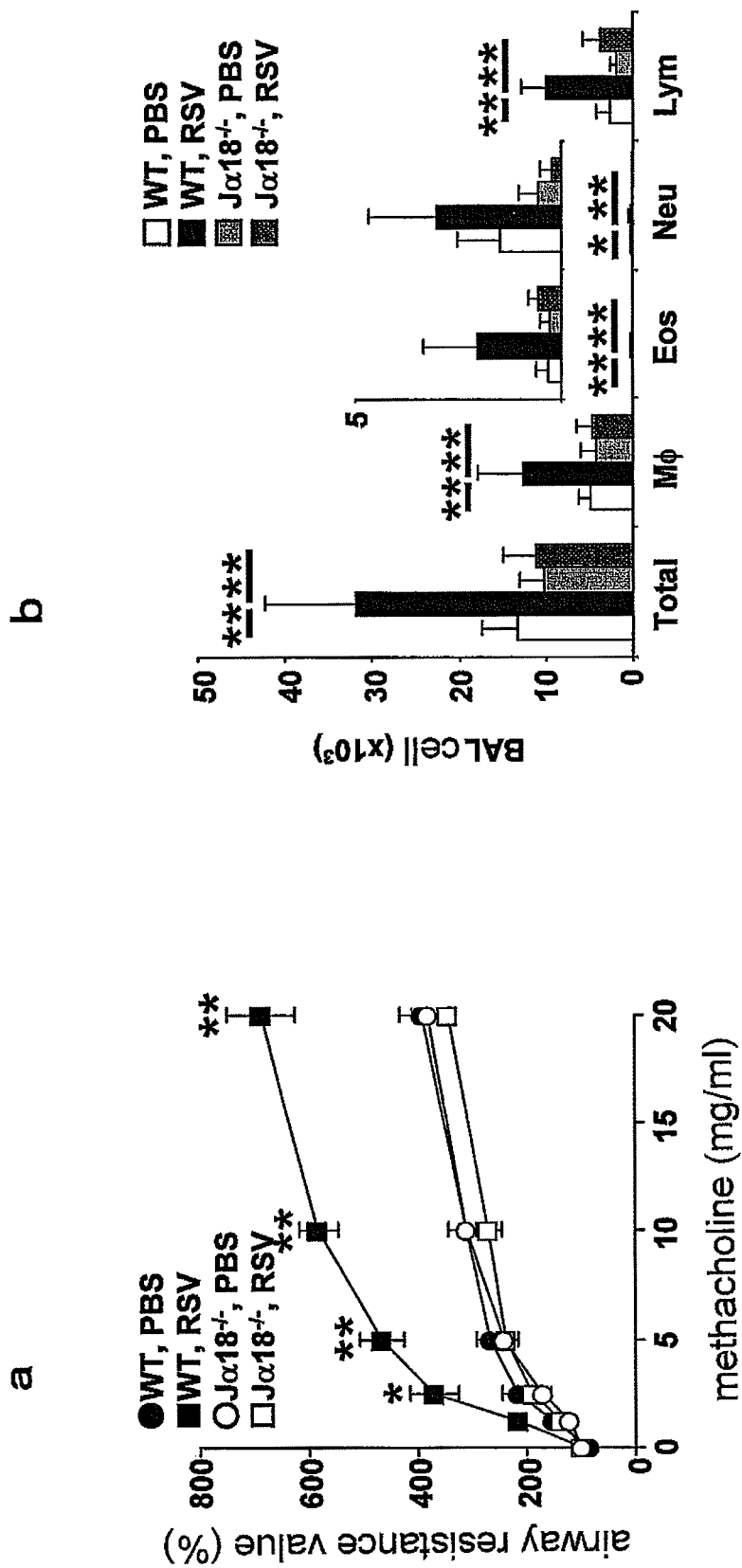
FIG. 27 is a view showing involvement of an IL-17RB positive NKT cell in RSV-dependent airway hypersensitivity pathogenesis.
Figure 28:
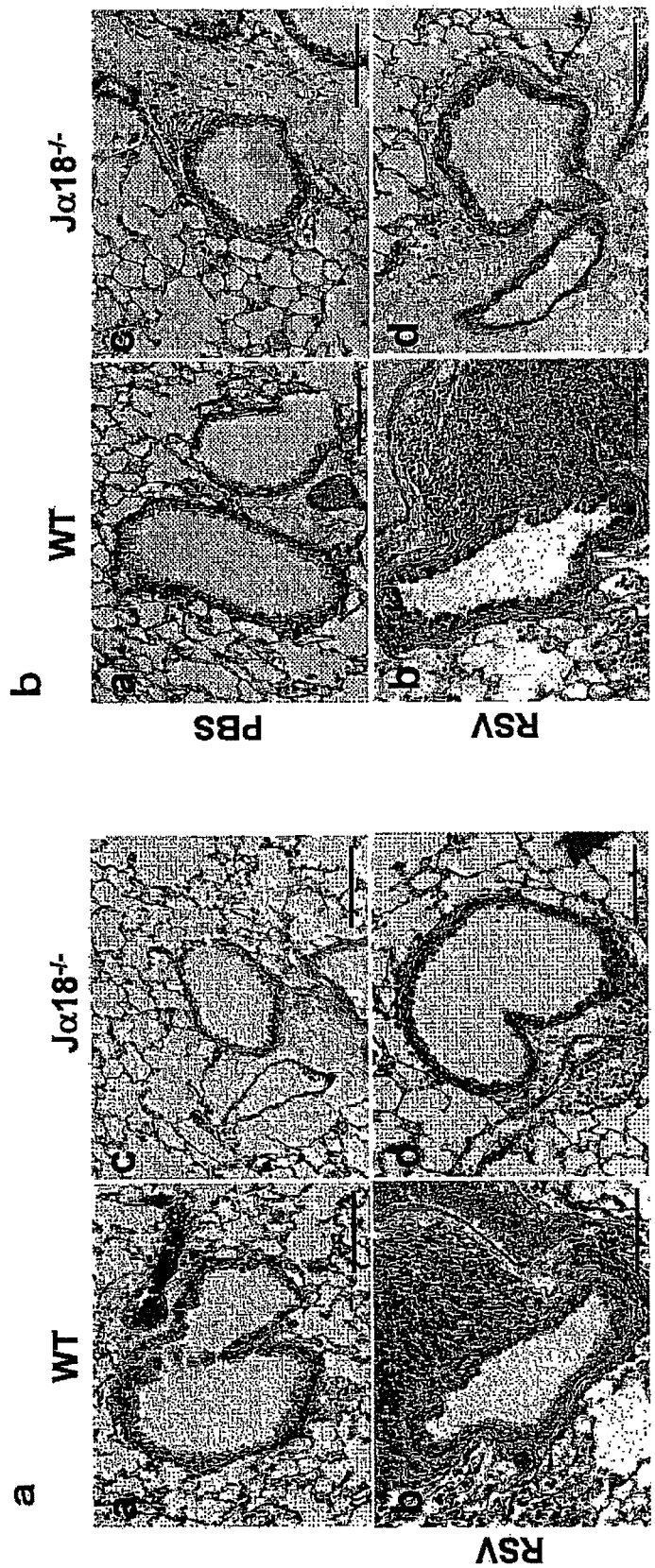
FIG. 28 is a view showing involvement of an IL-17RB positive NKT cell in RSV-dependent airway hypersensitivity pathogenesis.

Elucidation of a Role of the IL-17RB Positive NKT Cell in RS Virus-Dependent Airway Hypersensitivity Pathogenesis RS virus (respiratory syncytial virus: RSV) is a main causal virus of a baby acute airway infection (bronchiolitis, pneumonia etc.). RS virus infects an airway through contact or airborne droplet, after a latent stage for 2 to 5 days, a disease is developed with fever, snivel, and cough, and is usually relieved in one to two weeks, but in a small baby of two years old or younger, a disease frequently develops from upper respiratory inflammation to lower respiratory inflammation, developing bronchiolitis and pneumonia, and an immunodeficient infant, a low birth weight infant, and a small infant having a basic disease in respiratory apparatus/circulatory organ easily become serious, thus an attention is particularly necessary. There is no vaccine having an effect on the RSV infection and, in many cases, symptomatic treatment suppressing symptom is used. Using an alveolus washing solution of the RSV-infected mouse, a cytokine contained in the washing solution was investigated. IL-25, IL-6, IL-4 and IL-13 concentrations were measured by an ELISA method using an antibody of each cytokine/chemokine. IL-25 was induced early in an alveolus fluid by the RSV infection (FIG. 24). This is earlier than IL-13/IL-4 which is a Th2 cytokine, and IL-6 which is an inflammatory cytokine (FIG. 24). In addition, when a ratio of an NKT cell in an alveolus washing solution was investigated, it was found out that an NKT cell infiltrates into an alveolus washing solution by the RSV infection (FIG. 25). From these results, involvement of the IL-17RB positive NKT cell in RSV-dependent airway hypersensitivity pathogenesis was analyzed. In the airway inflammation pathogenesis model of OVA-alum described in Example 11, a mouse was infected three times 3 days before OVA/alum immunization, and development was observed by evocation with OVA. A series of protocol is shown in FIG. 26. As a result, it was revealed that all of increase in an airway pressure (FIG. 27a), cell infiltration into an alveolus fluid (FIG. 27b), infiltration of eosinophil/neutrophil (FIG. 28a), and mucin overproduction (FIG. 28b) are exacerbated in an NKT cell-deficient mouse than in a Balb/c mouse. These results strongly suggest that, in airway hypersensitivity pathogenesis with RSV, the IL-17RB positive NKT cell involves in its exacerbation.

This application is based on a patent application No. 2007-307981 filed in Japan, the contents of which are encompassed in full in the present specification.

Sequence Listing Free Text

SEQ ID NO: 3 fusion protein of extracellular domain of IL-17RB and Fc region of human IgG1
SEQ ID NO: 4 fusion protein of extracellular domain of IL-17RB and Fc region of human IgG1
SEQ ID NO: 5 PCR primer for detection of IFN-γ (sense)
SEQ ID NO: 6 PCR primer for detection of IFN-γ (antisense)
SEQ ID NO: 7 PCR primer for detection of IFN-γR (sense)
SEQ ID NO: 8 PCR primer for detection of IFN-γR (antisense)
SEQ ID NO: 9 PCR primer for detection of IL-12Rβ2 (sense)
SEQ ID NO: 10 PCR primer for detection of IL-12Rβ2 (antisense)
SEQ ID NO: 11 PCR primer for detection of IL-18Rβ (sense)
SEQ ID NO: 12 PCR primer for detection of IL-18Rβ (antisense)
SEQ ID NO: 13 PCR primer for detection of STAT4 (sense)
SEQ ID NO: 14 PCR primer for detection of STAT4 (antisense)
SEQ ID NO: 15 PCR primer for detection of T-bet (sense)
SEQ ID NO: 16 PCR primer for detection of T-bet (antisense)
SEQ ID NO: 17 PCR primer for detection of IL-4 (sense)
SEQ ID NO: 18 PCR primer for detection of IL-4 (antisense)
SEQ ID NO: 19 PCR primer for detection of IL-5 (sense)
SEQ ID NO: 20 PCR primer for detection of IL-5 (antisense)
SEQ ID NO: 21 PCR primer for detection of IL-10 (sense)
SEQ ID NO: 22 PCR primer for detection of IL-10 (antisense)
SEQ ID NO: 23 PCR primer for detection of IL-13 (sense)
SEQ ID NO: 24 PCR primer for detection of IL-13 (antisense)
SEQ ID NO: 25 PCR primer for detection of STAT6 (sense)
SEQ ID NO: 26 PCR primer for detection of STAT6 (antisense)
SEQ ID NO: 27 PCR primer for detection of GATA3 (sense)
SEQ ID NO: 28 PCR primer for detection of GATA3 (antisense)
SEQ ID NO: 29 PCR primer for detection of GranzymeA (sense)
SEQ ID NO: 30 PCR primer for detection of GranzymeA (antisense)
SEQ ID NO: 31 PCR primer for detection of Perforin1 (sense)
SEQ ID NO: 32 PCR primer for detection of Perforin1 (antisense)
SEQ ID NO: 33 PCR primer for detection of Klra7 (sense)
SEQ ID NO: 34 PCR primer for detection of Klra7 (antisense)
SEQ ID NO: 35 PCR primer for detection of Klrc1 (sense)
SEQ ID NO: 36 PCR primer for detection of Klrc1 (antisense)
SEQ ID NO: 37 PCR primer for detection of Klrd1 (sense)
SEQ ID NO: 38 PCR primer for detection of Klrd1 (antisense)
SEQ ID NO: 39 PCR primer for detection of Klrg1 (sense)
SEQ ID NO: 40 PCR primer for detection of Klrg1 (antisense)
SEQ ID NO: 41 PCR primer for detection of CXCR6 (sense)
SEQ ID NO: 42 PCR primer for detection of CXCR6 (antisense)
SEQ ID NO: 43 PCR primer for detection of CCR4 (sense)
SEQ ID NO: 44 PCR primer for detection of CCR4 (antisense)

SEQ ID NO: 45 PCR primer for detection of TARC/CCL17 (sense)
SEQ ID NO: 46 PCR primer for detection of TARC/CCL17 (antisense)
SEQ ID NO: 47 PCR primer for detection of MDC/CCL22 (sense)
SEQ ID NO: 48 PCR primer for detection of MDC/CCL22 (antisense)
SEQ ID NO: 49 PCR primer for detection of IL-17A (sense)
SEQ ID NO: 50 PCR primer for detection of IL-17A (antisense)
SEQ ID NO: 51 PCR primer for detection of RORγt (sense)
SEQ ID NO: 52 PCR primer for detection of RORγt (antisense)

---

The invention claimed is:

1. A method for inhibiting allergic airway inflammation and/or allergic airway hypersensitivity in a subject comprising (a) determining that the subject has an IL-17RB positive NKT cell and then (b) administering an effective amount of an antagonistic antibody to IL-17RB to the subject having the IL-17RB positive NKT cell, thereby inhibiting allergic airway inflammation and/or allergic airway hypersensitivity in the subject.

2. The method of claim 1, wherein allergic airway inflammation is inhibited in the subject.

3. The method of claim 1, wherein allergic airway hypersensitivity is inhibited in the subject.

4. The method of claim 1, wherein allergic airway inflammation and allergic airway hypersensitivity are inhibited in the subject.

5. A method for inhibiting eosinophilia in a subject comprising (a) determining that the subject has an IL-17RB positive NKT cell and then (b) administering an effective amount of an antagonistic antibody to IL-17RB to the subject having the IL-17RB positive NKT cell, thereby inhibiting eosinophilia in the subject.

* * * * *